(12) United States Patent
Chanda et al.

(10) Patent No.: US 10,312,389 B2
(45) Date of Patent: Jun. 4, 2019

(54) OPTICAL DETECTOR DEVICE WITH PATTERNED GRAPHENE LAYER AND RELATED METHODS

(71) Applicant: UNIVERSITY OF CENTRAL FLORIDA RESEARCH FOUNDATION, INC., Orlando, FL (US)

(72) Inventors: Debashis Chanda, Oviedo, FL (US); Alireza Safaei, Orlando, FL (US); Michael Leuenberger, Orlando, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 25 days.

(21) Appl. No.: 15/782,948

(22) Filed: Oct. 13, 2017

(65) Prior Publication Data

US 2018/0106933 A1 Apr. 19, 2018

Related U.S. Application Data

(60) Provisional application No. 62/407,596, filed on Oct. 13, 2016.

(51) Int. Cl.
| | |
|---|---|
| *H01L 31/0352* | (2006.01) |
| *G02B 5/12* | (2006.01) |
| *H01L 31/101* | (2006.01) |
| *H01L 31/0232* | (2014.01) |
| *H01L 31/09* | (2006.01) |

(Continued)

(52) U.S. Cl.
CPC ... *H01L 31/035209* (2013.01); *G01N 21/553* (2013.01); *G02B 5/008* (2013.01); *G02B 5/0866* (2013.01); *G02B 5/12* (2013.01); *H01L 27/307* (2013.01); *H01L 31/0232* (2013.01); *H01L 31/0328* (2013.01); *H01L 31/09* (2013.01); *H01L 31/101* (2013.01); *H01L 51/42* (2013.01); *B82Y 20/00* (2013.01); *B82Y 30/00* (2013.01);

(Continued)

(58) Field of Classification Search
CPC . H01L 51/42; H01L 31/0232; H01L 31/0344; H01L 31/035209–31/035227
See application file for complete search history.

(56) References Cited

U.S. PATENT DOCUMENTS

| | | | |
|---|---|---|---|
| 8,471,237 B2* | 6/2013 | Okai | H01L 21/2855 257/621 |
| 2010/0032548 A1* | 2/2010 | Murata | H01L 27/305 250/206 |
| 2014/0319357 A1* | 10/2014 | Ogawa | G01J 1/0429 250/349 |

FOREIGN PATENT DOCUMENTS

WO    WO-2015159080 A1 * 10/2015 ............. B82Y 10/00

OTHER PUBLICATIONS

Koppens et al. 2011 Graphene plasmonics: a platform for strong light-matter interactions.

(Continued)

*Primary Examiner* — Laura M Menz
*Assistant Examiner* — Candice Chan
(74) *Attorney, Agent, or Firm* — Allen, Dyer, Doppelt + Gilchrist, PA

(57) ABSTRACT

An optical detector device may include a substrate, a reflector layer carried by the substrate, and a first dielectric layer (Continued)

over the reflector layer. The optical detector device may include a graphene layer over the first dielectric layer and having a perforated pattern.

20 Claims, 15 Drawing Sheets

(51) Int. Cl.
  *H01L 51/42*   (2006.01)
  *G01N 21/552*  (2014.01)
  *H01L 31/0328* (2006.01)
  *G02B 5/00*   (2006.01)
  *G02B 5/08*   (2006.01)
  *H01L 27/30*  (2006.01)
  *G01N 21/77*  (2006.01)
  *B82Y 20/00*  (2011.01)
  *B82Y 30/00*  (2011.01)

(52) U.S. Cl.
  CPC ... *G01N 21/554* (2013.01); *G01N 2021/7773* (2013.01)

(56) References Cited

OTHER PUBLICATIONS

Kumar et al. 2013 Third harmonic generation in graphene and few-layer graphite films.
Hong et al. 2013 Optical third-harmonic generation in graphene.
Li et al. 2014 Refractory plasmonics with titanium nitride: broadband metamaterial absorber.
Gwinner et al. 2009 Periodic Large-Area Metallic Split-Ring Resonator Metamaterial Fabrication Based on Shadow Nanosphere Lithography.
Low et al. 2017 Polaritons in layered two-dimensional materials.
Gao et al. 2013 Excitation and active control of propagating surface plasmon polaritons in graphene.
Jnawali et al. 2013 Observation of a transient decrease in terahertz conductivity of single-layer graphene induced by ultrafast optical excitation.
Crassee et al. 2012 Intrinsic terahertz plasmons and magnetoplasmons in large scale monolayer graphene.
Ren et al. 2012 Terahertz and infrared spectroscopy of gated large-area graphene.
Vial et al. 2007 Description of dispersion properties of metals by means of the critical points model and application to the study of resonant structures using the FDTD method.
Bludov et al. 2013 A primer on surface plasmon-polaritons in graphene.
Mikhailov et al. 2008 Nonlinear electromagnetic response of graphene: frequency multiplication and the self-consistent-field effects.
Brown et al. 2013 Surface-enhanced infrared absorption using individual cross antennas tailored to chemical moieties.
Mikhailov 2007 Non-linear electromagnetic response of graphene.
Crozier et al. 2007 Experimental measurement of the dispersion relations of the surface plasmon modes of metal nanoparticle chains.
Yen et al. 2011 Infrared spectroscopy of wafer-scale graphene.
Papasimakis et al. 2010 Graphene in a photonic metamaterial.
Stauber 2014 Plasmonics in Dirac systems: from graphene to topological insulators.
Grigorenko et al. 2012 Graphene plasmonics.
Luo et al. 2013 Plasmons in graphene: recent progress and applications.
Shekhar et al. 2014 Hyperbolic metamaterials: fundamentals and applications.
Zhang et al. 2010 Electromagnetically induced transparency in metamaterials at near-infrared frequency.
Dai et al. 2015 Graphene on hexagonal boron nitride as a tunable hyperbolic metamaterial.
Nikitin et al. 2014 Efficient coupling of light to graphene plasmons by compressing surface polaritons with tapered bulk materials.

* cited by examiner

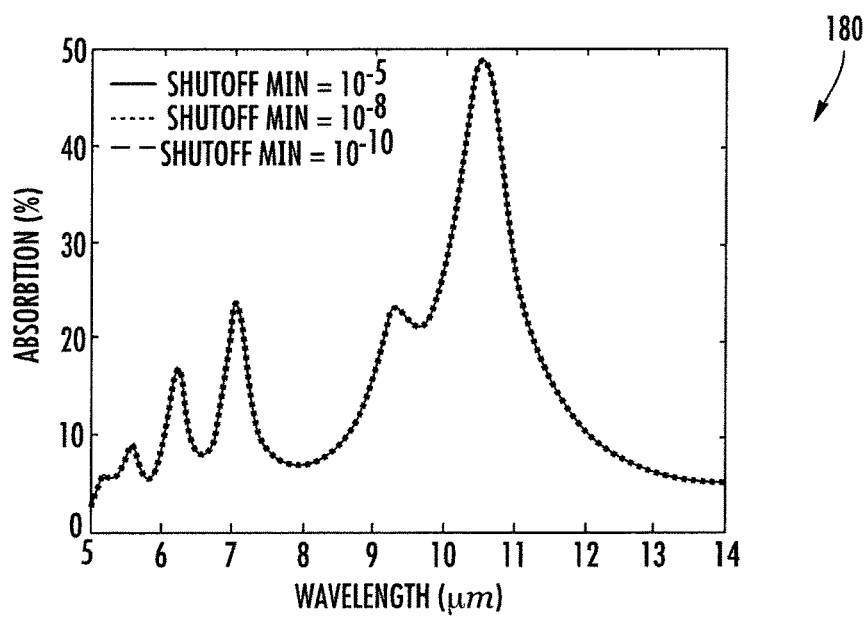
FIG. 10
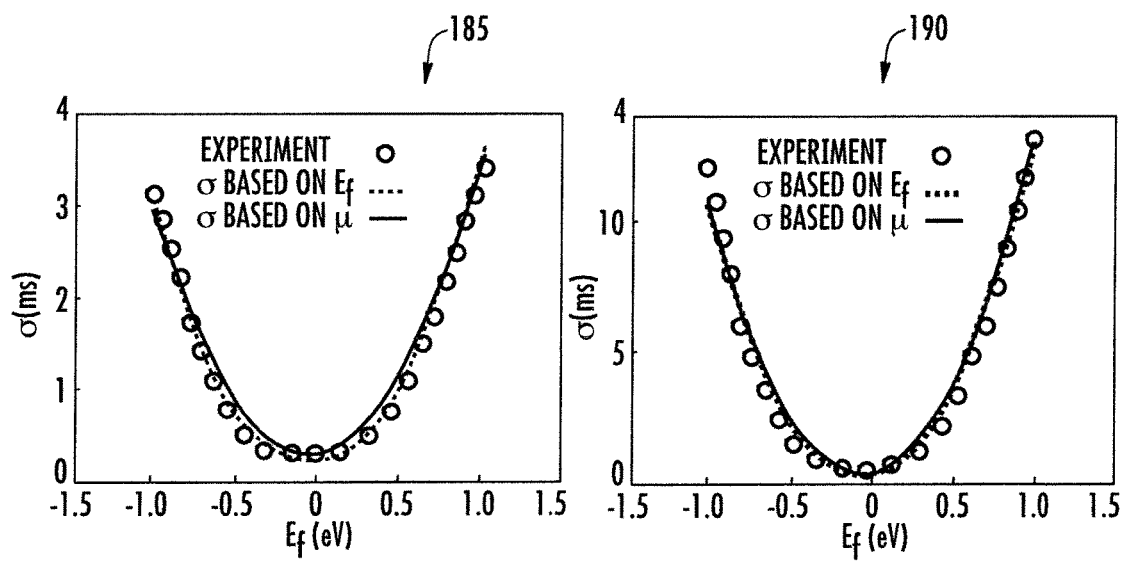
FIG. 11a
FIG. 11b

OPTICAL DETECTOR DEVICE WITH PATTERNED GRAPHENE LAYER AND RELATED METHODS

GOVERNMENT RIGHTS

This invention was made with Government support under contract No. HR0011-16-1-0003, awarded by the Department of Defense. The Government has certain rights in this invention.

RELATED APPLICATION

This application is based upon prior filed Application No. 62/407,596 filed Oct. 13, 2016, the entire subject matter of which is incorporated herein by reference in its entirety.

TECHNICAL FIELD

The present disclosure relates to the field of electro-optics, and, more particularly, to an optical detector device and related methods.

BACKGROUND

Graphene, one of the widely studied two dimensional materials, comprises a single layer of carbon atoms in a honeycomb lattice. It has special electrical, optical, and mechanical properties due to its tunable band dispersion relation and atomic thickness. Because of its unique band structure, graphene possesses very high mobility and fast carrier relaxation time,[1-5] making it an attractive candidate for ultrafast electronics and optoelectronic devices such as transistors,[6] optical switches,[7-9] mid-infrared (mid-IR) photodetectors,[10] photovoltaic devices,[11] saturable absorbers and ultrafast lasers[12] etc. However, low optical absorbance (<2.5%) in the visible to IR wavelength range makes graphene an inefficient optical material. With such a low absorption cross-section, these approaches are not suitable for many applications.

SUMMARY

Generally speaking, an optical detector device may include a substrate, and a reflector layer carried by the substrate. The optical detector device may comprise a first dielectric layer over the reflector layer, and a graphene layer over the first dielectric layer and having a perforated pattern therein.

In some embodiments, the perforated pattern may comprise a square array of openings. For example, each of the openings may be circle-shaped. The perforated pattern may be symmetrical. The first dielectric layer may have a polymer material. The graphene layer may include a monolayer of graphene.

Also, the optical detector device may also include a second dielectric layer over the graphene layer, a first electrically conductive contact coupled to the second dielectric layer, and a second electrically conductive contact coupled to the graphene layer. The reflector layer may comprise gold material. The reflector layer may have a thickness greater than a threshold thickness for optical opacity.

Another aspect is directed to a method for making an optical detector device. The method may include forming a reflector layer carried by a substrate, forming a first dielectric layer over the reflector layer, and forming a graphene layer over the first dielectric layer and having a perforated pattern therein.

BRIEF DESCRIPTION OF THE DRAWINGS

FIG. 10 is a diagram of light absorption of cavity coupled patterned graphene with cavity thickness of L=1400 nm, Period=400 nm, Diameter=330 nm, E_f=1.0 eV and μ=960 cm^2/(V·s) for different auto shutoff mins, according to the present disclosure.

FIGS. 11a-11b are diagrams of electrical conductivity of monolayer graphene sheets with different carrier mobilities, according to the present disclosure.

DETAILED DESCRIPTION

Figures 1A, 1B:
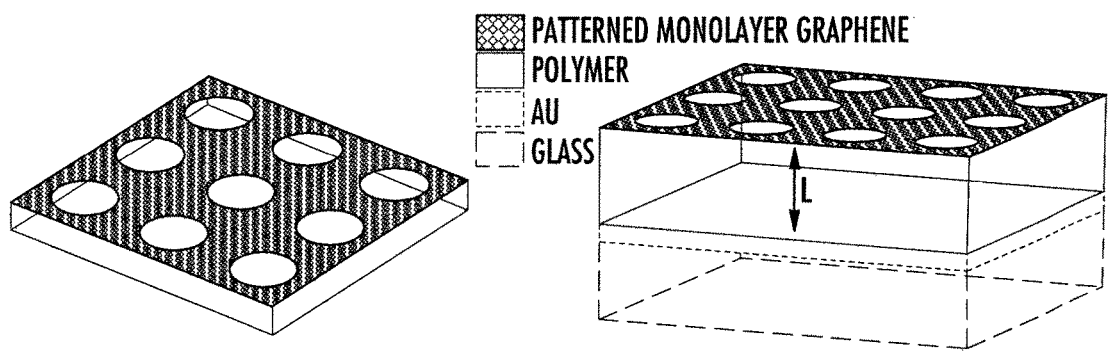
FIGS. 1a and 1b are schematic diagrams of a nanomesh device and a cavity-coupled nanomesh graphene, respectively, according to the present disclosure.

The present disclosure will now be described more fully hereinafter with reference to the accompanying drawings, in which several embodiments of the invention are shown. This present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art. Like numbers refer to like elements throughout, and base 100 reference numerals are used to indicate similar elements in alternative embodiments.

Unless graphene's absorption cross-section is dramatically enhanced, graphene will remain a scientific marvel without any practical optoelectronic use. An optical detector device may include a nanomesh monolayer graphene on a dielectric layer, and a gold reflector layer under the dielectric layer. The perforated pattern may include a square hole array.

Although graphene's high mobility is attractive for electronic devices, the low optical absorbance along with absence of a band gap is a serious obstacle for using graphene in optoelectronic systems. Here, Applicants show that it is possible to increase the light-graphene interaction and thereby enhance direct light absorption in mono-layer graphene from a low number (<2.5%) up to the unprecedented value of 60% in the mid infrared (IR) spectral domain by means of direct excitation of graphene plasmons that are coupled to an optical cavity without using any extraneous material. The formation of a square lattice of holes on graphene following a simple nanoimprinting technique not only preserves material continuity for electronic conductivity, which is essential for optoelectronic devices, but also leads to direct plasmon excitation that is independent of the incident light polarization.

Moreover, by shifting the Fermi energy and thus the density of the electrons electrostatically, the absorption band is shown to tune over a much wider range than previous demonstrations. Applicants developed an analytical model that considered the effects of the electron-phonon interaction between the substrate/graphene phonons and the electrons on the graphene, giving rise to a modified plasmon-phonon dispersion relation which resulted in accurate correspondence between theoretical predictions and experimental observations. The engineered plasmon-phonon interaction decreases the edge scattering of the carriers, which increases the plasmon lifetime. Applicants experimentally showed that the enhanced absorption is minimally affected by the carrier mobility that is further tunable with gate voltage and cavity length. Such gate voltage and cavity tunable enhanced absorption paves the path towards ultrasensitive infrared photodetection, optical modulation and other optoelectronic applications using monolayer of graphene.

Significance Statement

In this manuscript, Applicants report a direct absorption enhancement method based on cavity coupled patterned graphene whereby the Fermi energy is tuned by means of an external gate voltage, leading to a predicted maximum absorption of 60% and dynamic tunability up to 2 μm which closely corroborate experimentally measured absorption of ~45% and tunability up to 2 μm. Such high absorption and large spectral shift in monolayer graphene is observed, for the first time, due to the strong coupling between localized surface plasmon resonances on the nanomesh graphene and optical cavity modes. Such gate voltage and cavity tunable enhanced absorption paves the path towards ultrasensitive infrared photodetection, optical modulation and other optoelectronic applications using monolayer of graphene.

Introduction

Various strategies have been employed to amplify the light-matter interaction in graphene. Excitation of surface plasmon is one such technique where patterned graphene or patterned metal attached with a graphene is used to increase absorbance. In the first category of plasmonic enhancement, graphene nanoribbons[13-15] and nanodisks[16,17] results in an enhanced absorbance of 19% and 28%, respectively. However, the discontinuity of graphene nanoribbons/disks makes these structures impractical for optoelectronic devices. The second approach is based on plasmonic light focusing effect where some type of metal pattern is used to enhance the light graphene interactions[7,8,18-21]. However, with these indirect enhancement methods only a fraction of the absorption takes place in the graphene, and majority of the energy is absorbed as metal plasma loss defeating the purpose.

In contrast, Applicants employ a direct enhancement method based on cavity coupled patterned graphene whereby the Fermi energy is tuned by means of an external gate voltage, leading to a predicted maximum absorption of 60% and dynamic tunability up to 2 μm which closely corroborate experimentally measured absorption of ~45% and gate voltage controlled spectral shift of ~2 μm in monolayer graphene. Such high absorption and large spectral shift is observed due to the strong coupling between localized surface plasmon resonances on the nanomesh graphene and optical cavity modes. Unlike other metal pattern based plasmon excitations[7,8,18-21], this direct excitation of surface plasmon on graphene surface ensures 100% absorption in the monolayer graphene. Moreover, absence of impurities (metals) like other indirect absorption enhancement methods[7,8,18-21] ensures high carrier mobility.

Extraordinary Absorption Mechanism

At high EM wave frequencies in the visible domain $\hbar\omega \gg (E_F, k_B T)$ where $E_F$ is the Fermi energy with respect to the charge neutrality point (CNP) of the Dirac cone, interband transitions dominate and the light absorbance of graphene is $A=\pi\alpha \approx 2.3\%$, which is independent of wavelength ($\alpha \approx 1/137$ is the fine structure constant)[4]. However, in the mid-IR frequency range and for high Fermi energy $E_F \gg \hbar\omega$, graphene's optical response is dominated by intraband transitions and the conductivity (σ) follows the Drude-Lorentz model,[2-4] i.e.:

$$\sigma^{intra}(\omega) = \frac{ie^2 \frac{E_F}{\pi\hbar^2}}{\omega + i\tau^{-1}} \quad (1)$$

where τ is the relaxation time determined by impurity scattering ($\tau_{imp}$) and electron-phonon ($\tau_{el-ph}$) interaction time as $\tau^{-1}=\tau_{imp}^{-1}+\tau_{el-ph}^{-1}$ [22] (see SI).

An array of holes on graphene sheet not only conserves continuity of graphene, but also preserves the graphene dispersion relation and conductivity, as the edge-to-edge distance of the holes which is the shortest distance between two nearest neighbour holes is larger than the mean free path of electrons. The experimentally measured carrier mobilities before and after nanomesh formation was carried out to validate this assumption. By coupling this perforated graphene to an optical cavity, Applicants showed that it is possible to achieve constructive interference between incident and scattered electric fields, thereby enhancing the absorption on the graphene nanomesh. Moreover, this coupled system is able to amplify direct light absorbance in graphene even in conditions of low carrier mobility unlike other tecniques where a high carrier mobility is required for absorption enhancement. Exciting localized surface plasmon coupled to an optical cavity leads to strong light-matter interaction such that even in low carrier mobility condition the enhancement in absorption is large compare to pristine graphene.

The system consists of a dielectric slab with variable thickness L and refractive index $n_d$ of 1.56 sandwiched between a patterned graphene perforated with a square hole array with 330 nm diameter and 400 nm period and an optically thick (200 nm) gold back reflector as illustrated in FIGS. 1a-1d. These feature sizes are much larger than the previous 60-100 nm nanoribbon/disk patterns[16,17] and hence much easier to fabricate.

A simple embossing based nanoimprinting technique was followed to pattern the graphene. One such imprinting stamp can produce 1000's of imprints without any noticeable pattern degradation. Due to the symmetrical nanomesh square lattice pattern the excitation of LSPs is independent of light polarization for normal angle of incidence. The cavity thickness corresponding to a quarter wave position ($L=m\lambda/4n_{eff}$) intensifies the electric field on the graphene nanomesh due to the constructive interference between incident and reflected fields inducing about two order of magnitude higher absorption in graphene. Increasing the optical cavity thickness induces higher transverse cavity modes ($L=m\lambda/4n_{eff}$) where $n_{eff}$ is the effective refractive index of the dielectric slab modified by patterned graphene, which is calculated by means of the effective medium approach[23,24], λ, is the incident EM wavelength and m=[0, 1, 2, 3, . . . ] stands for the optical cavity m-th order. For odd/even cavity modes, the incoming and reflected electric fields interfere constructively/destructively at the position of the patterned graphene, thereby giving rise to a maximum/minimum value in the LSP-enhanced absorbance as can be observed from the FDTD prediction in FIG. 1d for graphene with electron mobility $\mu=960$ cm$^2$/(v·s) and Fermi energy $E_F=1$ eV excited with x-polarized light.

Figures 1C, 1D:
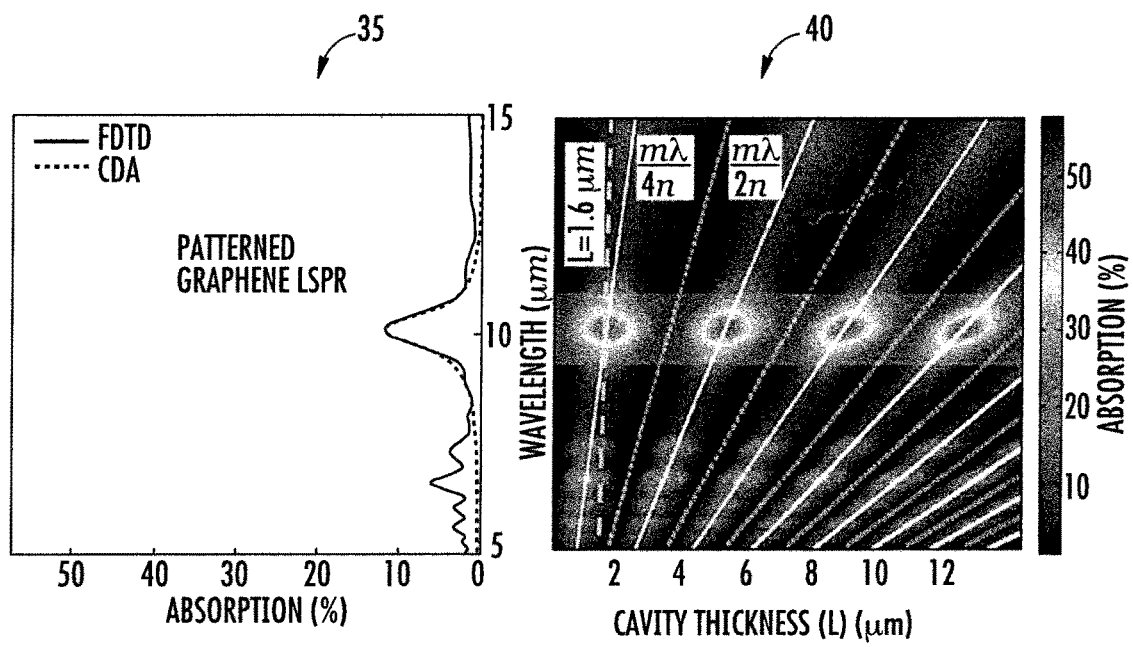
FIGS. 1c and 1d are diagrams of a finite-difference time domain (FDTD)/coupled dipole approximation (CDA) predicted absorption and a FDTD prediction of absorption as a function of cavity thicknesses for the cavity-coupled case, respectively, according to the present disclosure.
Figures 1E, 1F:
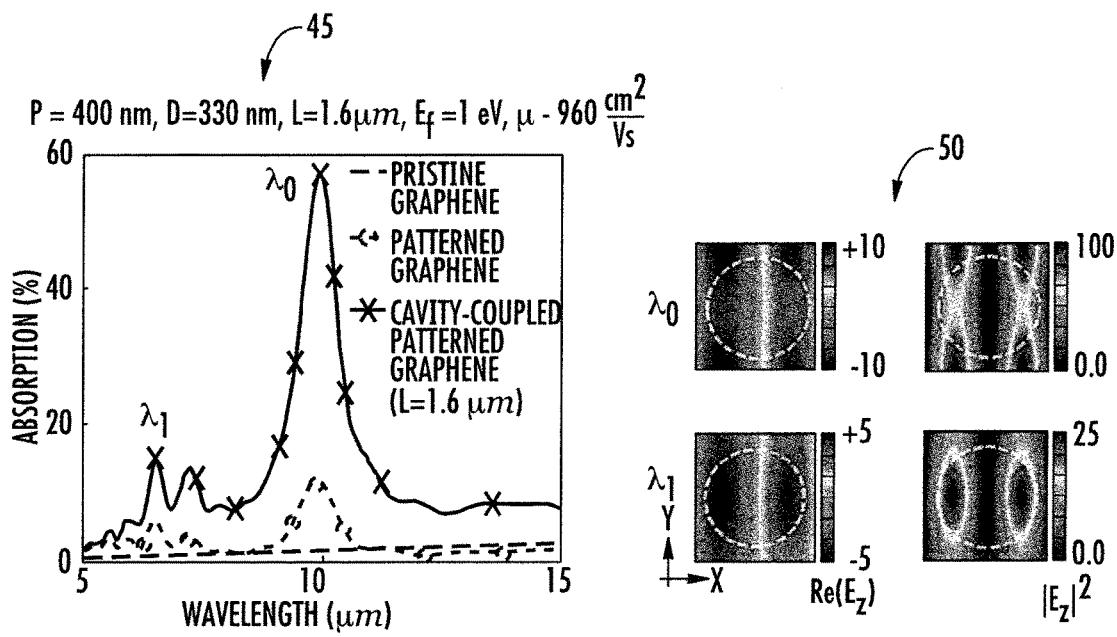
FIGS. 1e and 1f are diagrams of an optical absorption of an example patterned and cavity coupled patterned graphene and a FDTD predicted real part and intensity of electric field distribution in z-direction, respectively, according to the present disclosure.

The corresponding FDTD predicted absorption of the patterned graphene without optical cavity is shown in diagram 35 FIG. 1c. The analytical CDA[24,25] prediction is overlaid on top of the FDTD results. The close corrspondence between the FDTD and CDA vindicates the accuracy of the analytical predictions (see SI for the detailed CDA derivation). The solid white and dotted dark lines on FDTD prediction in diagram 40 of FIG. 1d show the analytical cavity modes dispersion as a function of wavelength and cavity thickness which accurately demonstrates the origin of this extraordinary absorption as temporal and spatial overlap between LSPR and cavity modes. Comparison between uncoupled and coupled systems (FIGS. 1c and 1d) clearly demonstrates that the optical cavity intensifies the surface plasmon fields without changing the LSP resonance frequencies for all cavity modes. FIG. 1e (diagram 45) compares FDTD predicted absorption in pristine graphene, patterned graphene and cavity-coupled patterned graphene. A cavity length of L=1.6 μm which satisfies the cavity resonance condition leads to ~60% light absorption around λ=10 μm, that constitutes about 30-fold absorption enhancement compare to pristine graphene. The corresponding real part (Re ($E_z$)) and intensity ($|E_z|^2$) of electric field distribution in z-direction is shown in diagram 50 of FIG. 1f, which reveals the dipolar nature of this plasmonic mode. The side coupling in the y-direction separates the LSP charges on the nanohole edges along the x-direction and pulls them towards the diagonal directions at 45° and −45° away from the x-axis. For sub-wavelength scale nearest-neighbour distance (~λ/30) between nanoholes, coupling between them occurs via near-field and far-field EM radiation. An optical cavity strengthens this coupling due to the enhancement of the total electric field intensity at the edges of nanoholes, which leads to a 5-fold increase in the optical absorption cross-section. From field distributions of two absorption peaks ($\lambda_0$ and $\lambda_1$) in FIG. if, it is evident that spatial and temporal overlap between plasmonic and photonic cavity modes leads to strong local field enahncement and subsequently enahnced absorption for $\lambda_0$ (see SI for details).

The Effects of Carrier Mobility on the Graphene Plasmons.

Due to the two-dimensional nature of graphene, surface charge impurities and defects substantially alter the mean free path of electrons, and therefore experimentally measured mobility (250-1000 cm$^2$/(v·s)) differs significantly from theoretically predicted range (2000-10000 cm$^2$/(v·s)).[26-28] For example, polymers used to transfer the graphene sheet, the fabrication of the pattern, the doping of the graphene sheet, and oxidation decrease the electron mobility. Typically graphene on a polymer substrate has a low carrier mobility[5,29] (<1000 cm$^2$/(v·s)) because of extra scattering processes. Typical scattering centers consist of charge impurities, polymers roughness, and coupling between graphene electrons and polar or non-polar optical phonons of the polymer matrix.[26-28] The reduced carrier mobility in graphene is reflected in the reduction of the momentum relaxation time (τ), which determines the plasmon lifetime and the absorption spectrum bandwidth. FIGS. 2a-2d (diagrams 55, 60, 65, 70) show the FDTD predicted absorption spectra of cavity-coupled nanomesh graphene for two different mobilities (p) of 960 cm$^2$/(v·s) and 250 cm$^2$/(v·s). For relatively high mobility (960 cm$^2$/(v·s)), loss is small and therefore the bandwidth of the absorption spectrum is narrow, indicating increased lifetime of plasmons as observed in FIGS. 2a-2b for a cavity thickness L=1.1 μm (this cavity thickness is chosen to capture high frequency weaker resonances).

In FDTD simulation, graphene (n,k) values were obtained from mobility as described in the SI. Higher loss in lower carrier mobility graphene gives rise to reduced plasmon lifetime and broadening of absorption spectrum which results in the merger of two principal plasmonic modes and the formation of an asymmetrical peak, as seen from FIGS. 2c-2d. The first maximum absorption happens at cavity thickness L=1.6 μm for the present geometry (FIG. 2c). The cavity mode dispersion as a function of cavity thickness dictates the absorption bandwidth and number of resonances over a specified spectral range (FIG. 2c). Although, the light absorption decreases from 45% to 38% due to the reduction in mobility from 960 cm²/(v·s) to 250 cm²/(v·s), it is still substantially larger than other strategies employed before in monolayer graphene.[13-17] The carrier mobility of graphene can be adjusted by reducing the number of scattering centers on the top and the bottom of the graphene sheet, which further provides the possibility to tune the absorption bandwidth and magnitude.

Nanoimprinted Cavity-Coupled Graphene.

Figure 3A:
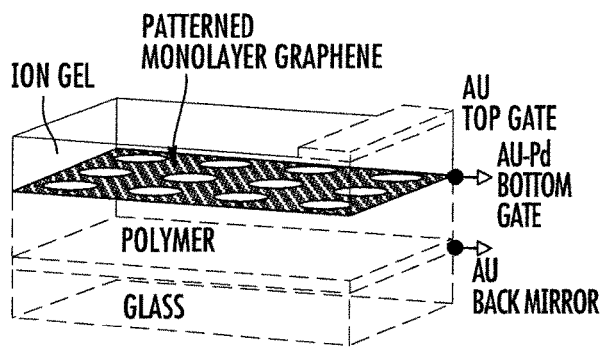
FIG. 3a is a schematic diagram of a graphene plasmonic-cavity structure, according to the present disclosure.

The schematic of the cavity-coupled nanostructured graphene architecture is shown in FIG. 3a. A nanoimprinting step is performed on a spin coated polymer layer (SU-8) on top of the graphene followed by $O_2$ plasma etch. Subsequent residual polymer removal steps complete the square array of nanohole formation on the graphene with period 400 nm and diameter 330 nm. Due to the support from both sides, the nanoimprinting technique does not create cracks on the mono-layer graphene. The PDMS nanoimprinting stamp is made from a direct laser written (DLW) master pattern. Once a master pattern is made that can produce 100's of polymeric imprinting stamps, and one such stamp can produce 1000's of imprints without any noticeable pattern degradation. This method paves the path towards low cost production of patterned graphene. Raman measurement in diagram 75 of FIG. 3b proves the presence of graphene before the nanomesh formation.

Figure 3B:
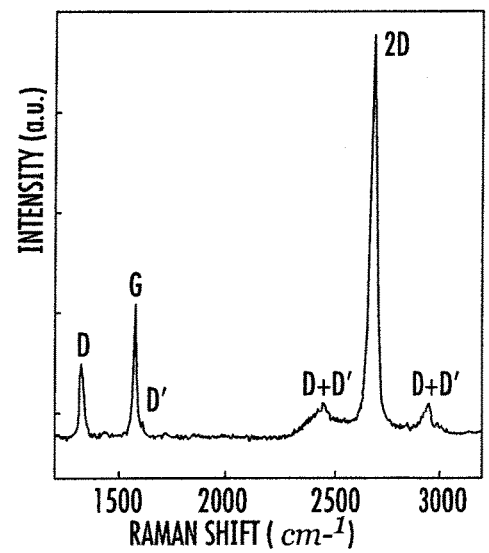
FIG. 3b is a diagram of a Raman spectrum of grown graphene, according to the present disclosure.
Figure 3C:
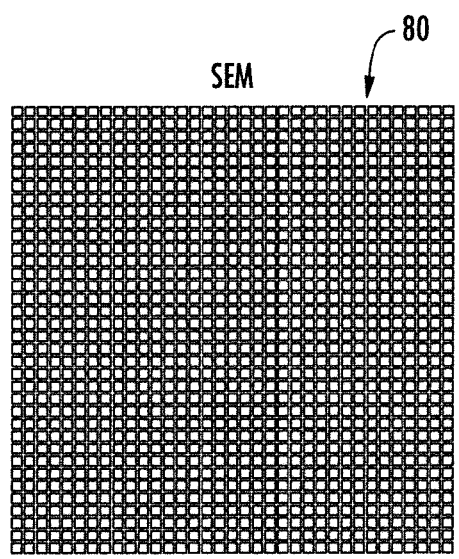
FIG. 3c is a scanning electron microscope (SEM) image of a fabricated perforated graphene sheet on polymeric substrate, according to the present disclosure.

The Raman spectrum exhibits typical bands for single layer graphene consisting of a G-band at ~1580 cm⁻¹, which is associated with doubly degenerate phonon mode ($E_{2g}$-symmetry) at the Γ point and originates from first-order Raman scattering due to the stretching of the C—C bond in the graphene, that is prevalent in all carbon materials with $sp^2$ bands. The weak D' peak arises from the hybridization of the G-peak, which happens when localized vibrational modes of the randomly distributed impurities in graphene interact with its extended phonon modes. The strong 2D peak located at ~2720 cm⁻¹ is a signature of graphitic $sp^2$ band materials, which is due to a second-order two-phonon scattering depending on the excitation laser frequency. The shape of the 2D band determines the number of graphene layers, i.e. for monolayer graphene it is sharper and more intense than the G-band in multilayer graphene[30-32]. Moreover, the D-band peak commonly appears around 1300-1400 cm⁻¹, which is the sign of defects and disorder in the $sp^2$ hybridized carbon structures. The D+D' and D+D" bands are for the substrate glass and polymer residue, respectively. This Raman measurement in FIG. 3b confirms that the grown graphene sheet is a monolayer with some distributed impurities and defects. Diagram 80 of FIG. 3c shows the scanning electron microscope (SEM) image of an nanoimprinted nanopatterned graphene showing good uniformity in nanohole diameter across the patterned film. In order to re-confirm the nanomesh formation a conductive atomic force microscopy (AFM) was performed which shows the holes in mono-layer graphene as a function of change in conductivity as shown in diagram 85 of FIG. 3d.

The Effect of Plasmon-Phonon Coupling.

The simple Drude model can not capture the plasmon-phonon interactions which leads to a discrepancy between FDTD predictions and experimental measurements. The interaction between substrate/graphene phonons and electrons in graphene leads to modification of the graphene plasmon dispersion relation, which determines the lifetime and the propagation distance of the surface plasmon polaritons (SPPs). This coupling gives rise to novel states and band gap in the plasmonic band structure[14,33-35].

According to the random phase approximation (RPA) for a two dimensional system such as graphene in quasistatic approximation, the plasma frequency is given by[36,37]

$$\omega_p(q) = \sqrt{\frac{2\pi n_e e^2}{m^* \varepsilon_d} q}, \tag{2}$$

where $n_e$, e and $m^*$ are electron density, charge, and effective mass in graphene, respectively. The plasmon wavevector of the nanomesh graphene (q) is the lowest quasistatic eigenmode $$q = q_1 \sim \frac{\pi}{w - w_0},$$

where w is the edge-to-edge distance of the holes and $w_0$ is the parameter that includes edge effects[14].

Figure 4A:
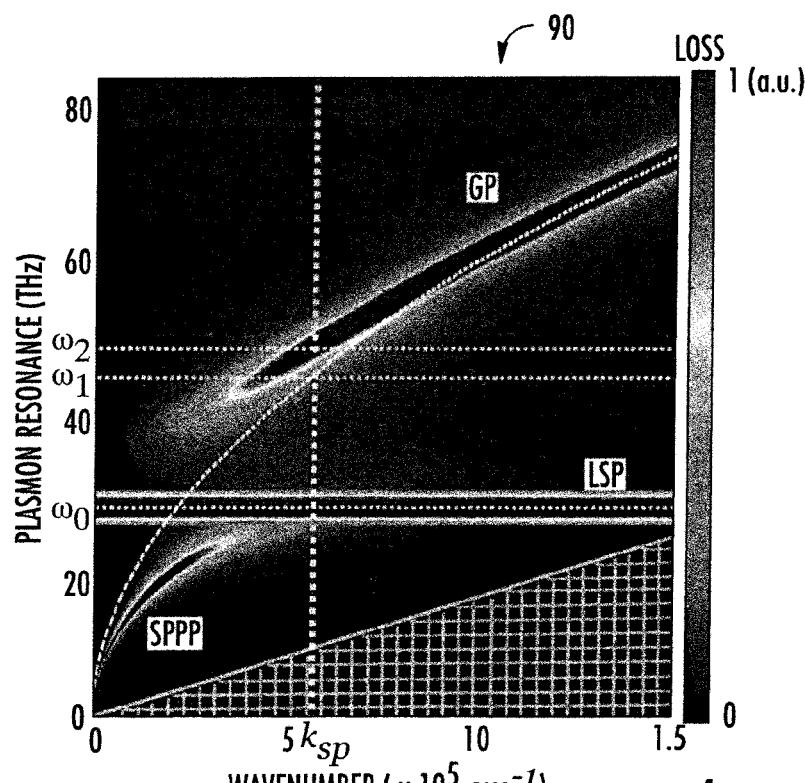
FIGS. 4a and 4b are diagrams of energy dispersion and wavelength dependent absorption in presence of substrate phonons, and experimental and theoretical prediction of the plasmon excitation on perforated graphene, respectively, according to the present disclosure.
Figures 7A, 7B:
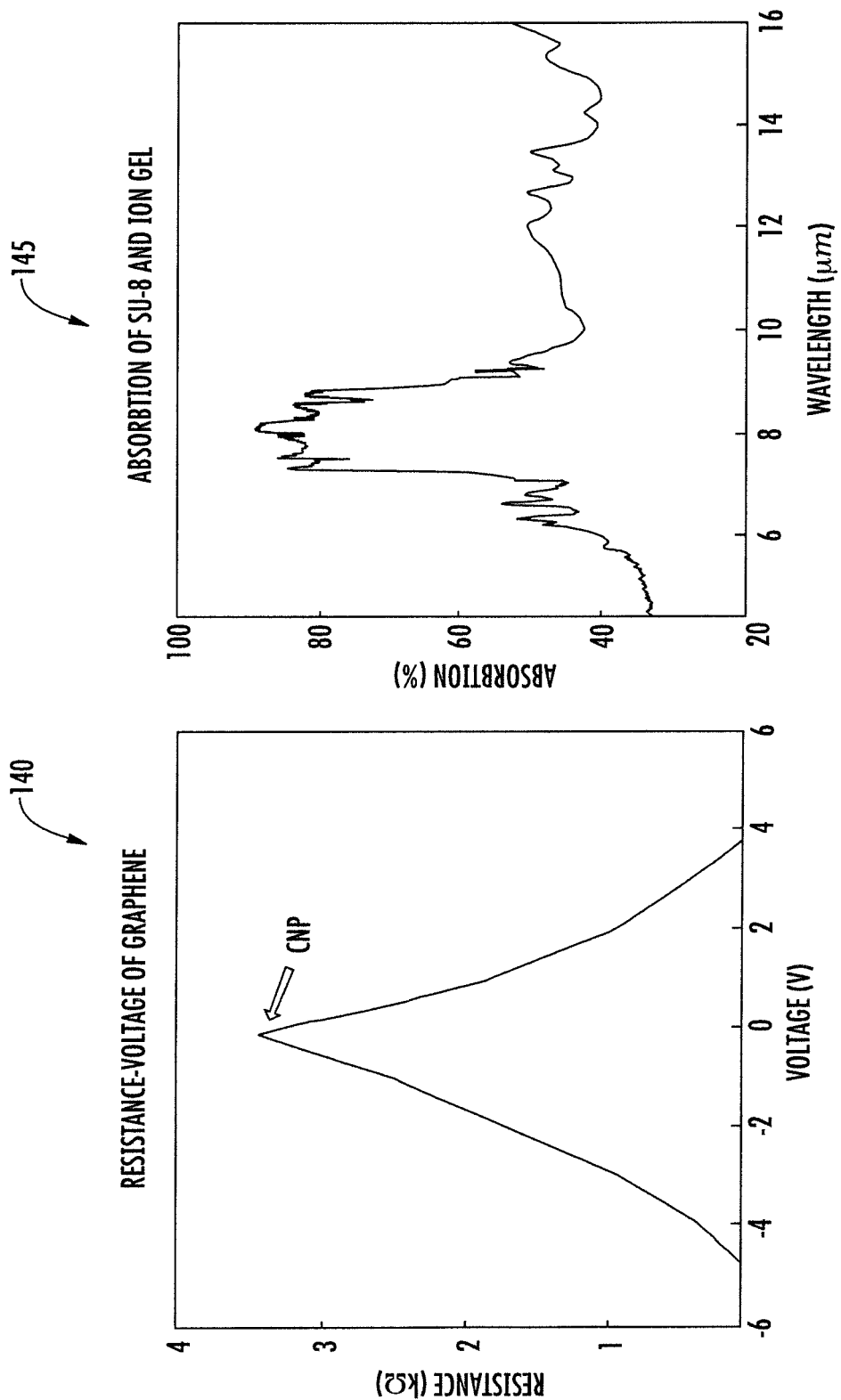
FIGS. 7a-7b are diagrams of doping of graphene sheet by using ion gel as a dielectric for the capacitor, and an experimental result for the light absorption of the compound of SU-8 and ion gel, according to the present disclosure.

By tracking the splitting of plasmon-phonon diagram and fitting the surface plasmon-phonon polariton (SPPP) and graphene plasmon (GP) branches to the experimental data in diagram 90 of FIG. 4a, Applicants estimated $w_0$=14 nm for the present w=70 nm. The white dotted curved line in FIG. 4a represents Eq. (2). A compound which consists of SU-8 as cavity spacer and ion-gel as gate dielectric layers have a longitudinal optical phonon at $\omega_{sp}$=36.21 THz with lifetime $\tau_{sp}$=2.42×10⁻¹³ s, as estimated from the absorption spectral peak location and bandwidth, respectively (FIG. 7b). The substrate optical phonon is coupled to graphene electrons by Fröhlich interaction, which leads to the hybridization of the substrate optical phonons and the graphene plasmons. This plasmon-phonon coupling can be characterised through the loss function (Z), which is the imaginary part of inverse effective dielectric function calculated via the generalized RPA theory[13,14]

$$Z = \mathfrak{I}\left(\frac{1}{\varepsilon_{eff}}\right) \tag{3}$$

The loss function represents the amount of energy dissipated by exciting the plasmon and coupling that to the substrate and graphene optical phonons. The details of the calculation are shown in the SI. FIG. 4a shows the loss function for graphene with mobility μ=960 cm²/(v·s) and $E_F$=1 eV. The plasmon assisted electron-hole pair generation in this structure is outside the Landau intraband damping region as shown as the shaded area in FIG. 4a, defined by $\hbar\omega/E_F<q/k_F$, where $k_F$ is the Fermi wavevector.[38] A band gap in the plasmon-phonon dispersion relation is formed via Fröhlich interaction between graphene plasmons and optical phonons. This coupling leads to the splitting of the energy into two distinct branches: surface plasmon phonon polaritons (SPPPs) and graphene phonons (GPs)[14,15] The horizontal branch line which is marked as $\omega_0$ is the localized surface plasmon mode ($\lambda_0$) in FIG. 1e, is independent of the plasmon wavevector. The asymmetric solid line shape of the first band in diagram 95 of FIG. 4b, which is observed in experiments, is due to the merging of these two bands.

Figure 4B:
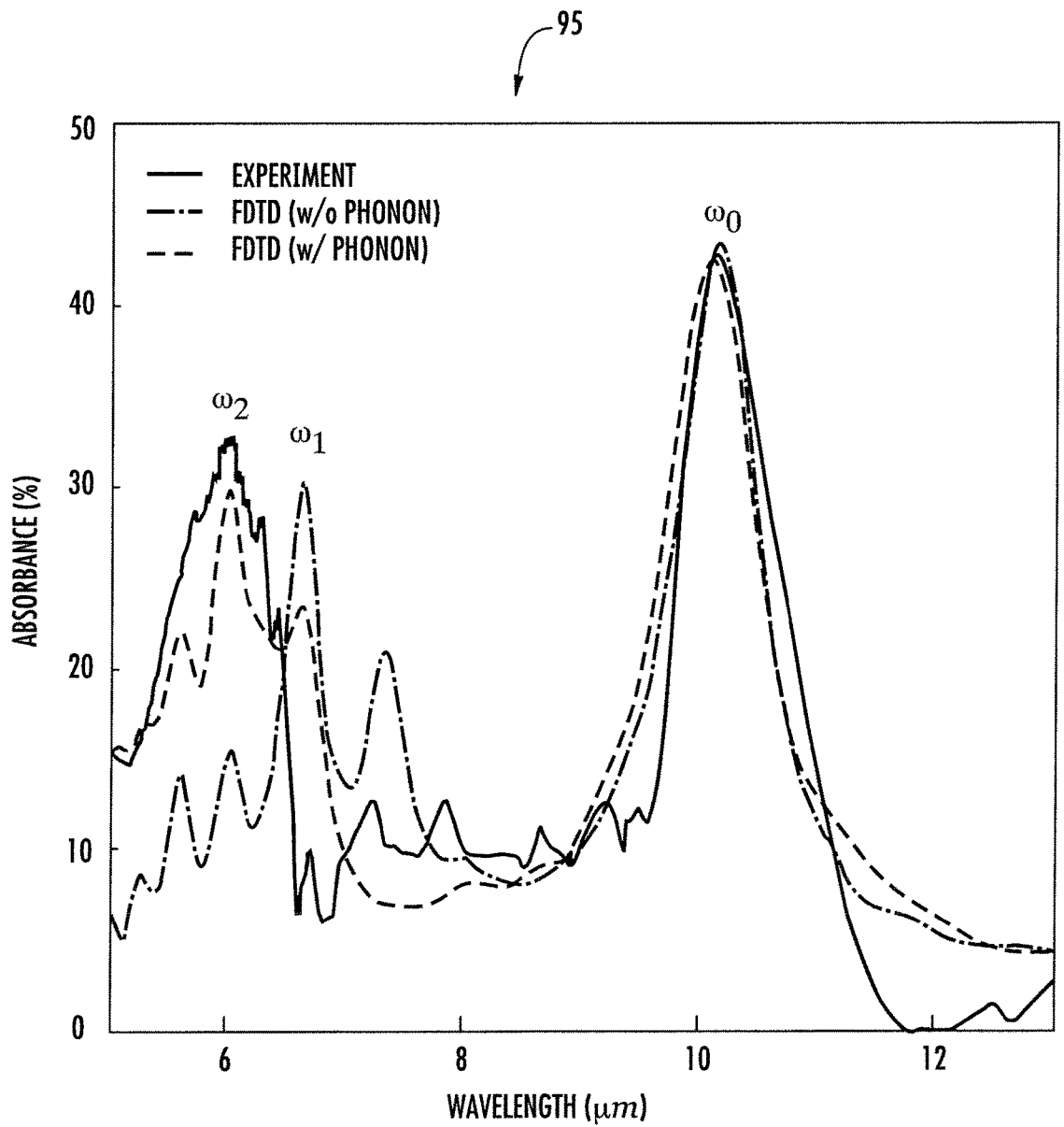

FIG. 4a shows a clear blue shift in the GP band at a wavevector ($k_{sp}$=5.62×10⁵ cm⁻¹) corresponding to w=70 nm which is edge-to-edge distance between the holes, stems from the plasmon-phonon coupling that gives rise to the discrepancy between $\omega_1$ and $\omega_2$ as evident in FIG. 4b. The slight discrepancy between the theoretical prediction and the experiment can be removed by inserting the plasmon-phonon interaction as perturbation and using $\varepsilon'^{pa}$ in the FDTD simulation as effective graphene dielectric function, thereby recovering the experimentally observed blue shift, as illustrated in the FIG. 4b by the red dotted line. The details of this derivation are given in the SI. The thickness of the optical cavity for the perforated graphene sheet with mobility $\mu$=960 cm$^2$/(v·s) is chosen to be 1.1 µm in order to illustrate that the first and second modes lead to 45% and 33% light absorption, respectively. This calculation proves that the plasmon-phonon interaction hybridizes the plasmon dispersion relation which leads to a blueshift in propagating surface plasmon spectrum. However, the main absorption peak ($\omega_0$) which originates from LSP remain unperturbed due to frequency domain seperation betweet phonon and LSP resonances.

Electronically Tunable Response.

Figure 5A:
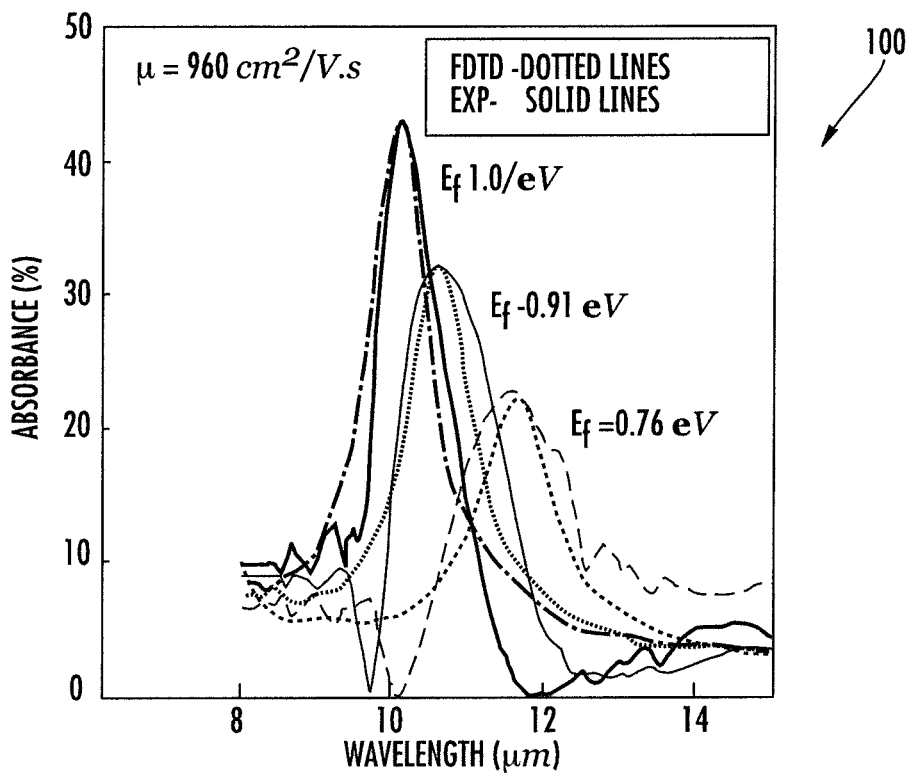
FIGS. 5a and 5c are diagrams of tunable absorption and absorption peak shift as a function of wavelength and Fermi energy (gate voltage) for high mobility mono-layer graphene, according to the present disclosure.
Figure 5B:
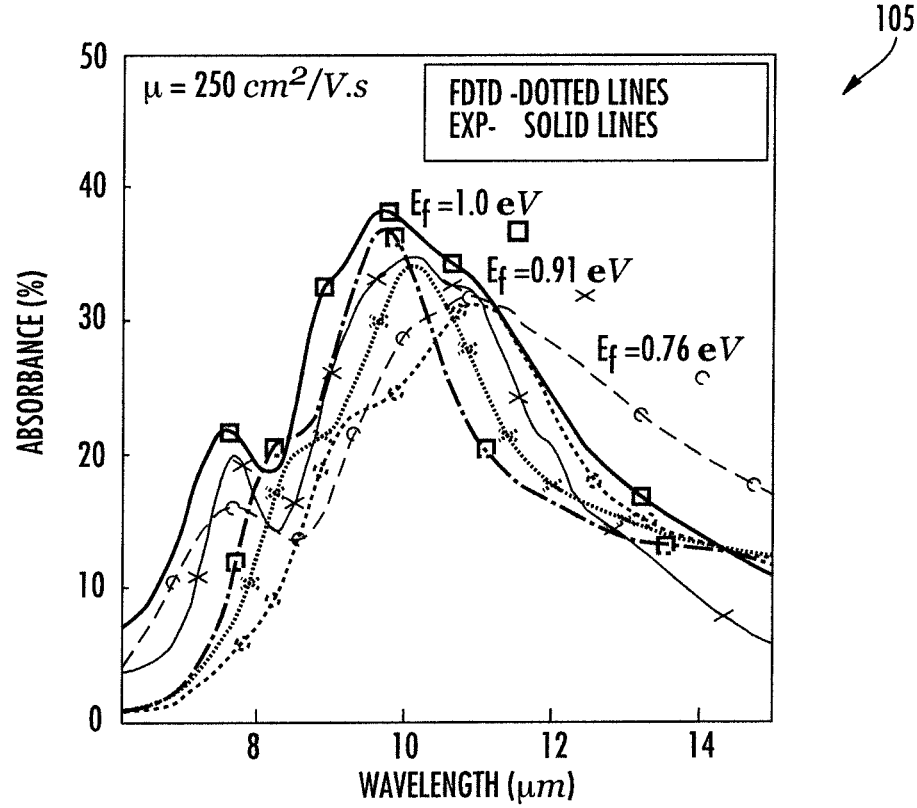
FIGS. 5b and 5d are diagrams of tunable absorption and absorption peak shift as a function of wavelength and Fermi energy (gate voltage) for low mobility mono-layer graphene, according to the present disclosure.
Figure 5C:
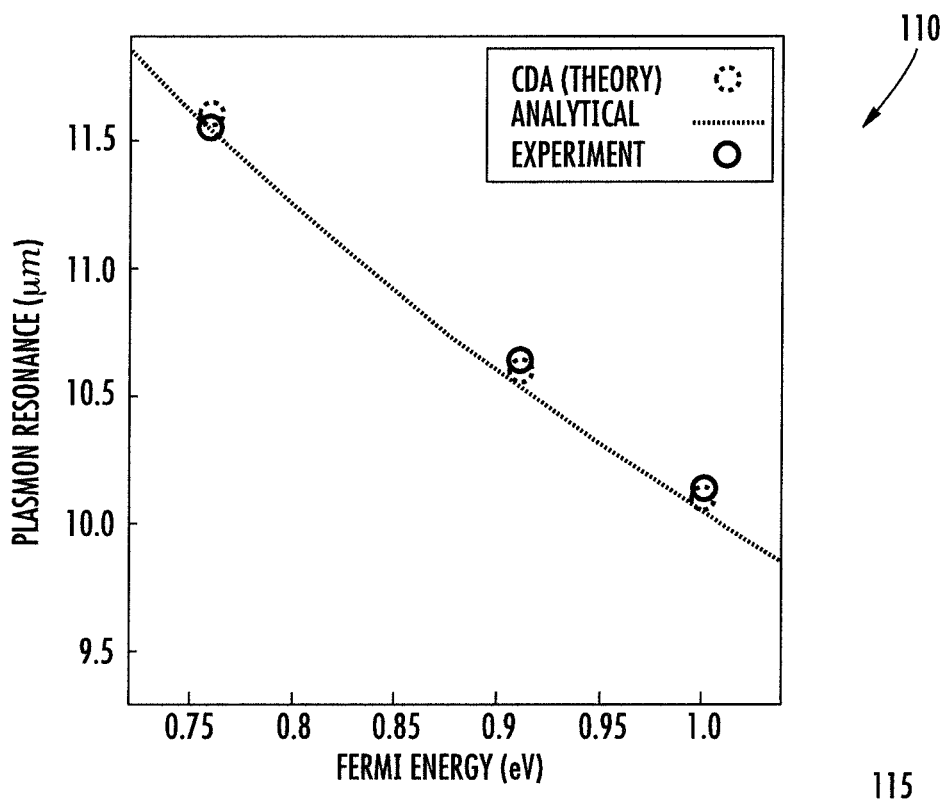
Figure 5D:
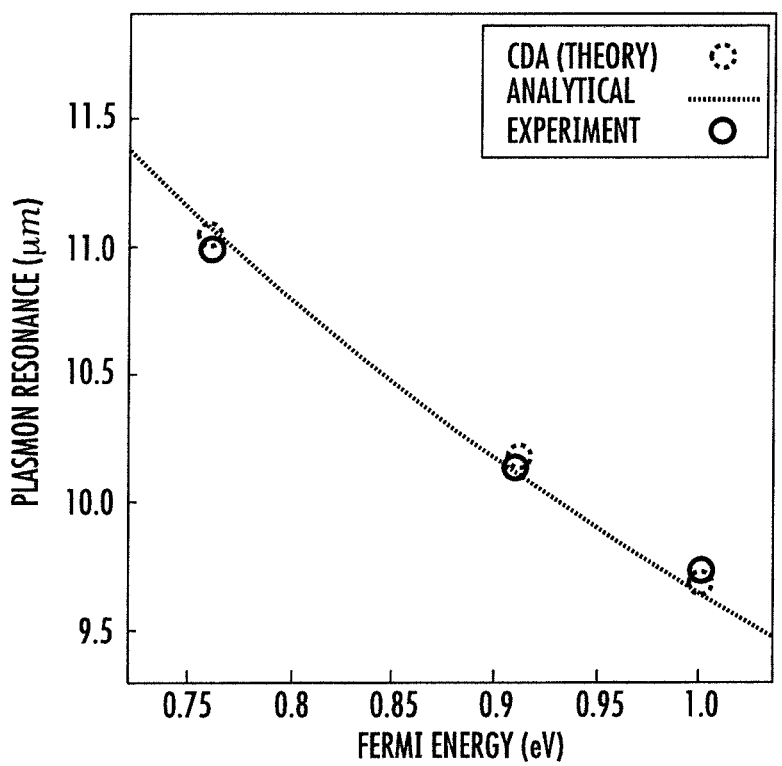

FIGS. 5a and 5b (diagrams 100, 105) show theoretical and experimental electronically tunable absorption in cavity-coupled graphene nanomesh with 400 nm period and 330 nm diameter for high (960 cm$^2$/v·s) and low (250 cm$^2$/v·s) mobilities, respectively. In both cases, Fermi energy was varied between 0.7 eV to 1 eV. The high and low mobility graphenes exhibit a large ~2 µm and ~1 µm electrostatic tunability as can be observed in FIG. 5a and FIG. 5b, respectively. According to the Drude model, the refractive index of high mobility graphene is more sensitive to change of Fermi energy than that of low mobility graphene. The smaller peak in FIG. 5b around 7.6 µm corresponds to polymer residue, which shows the effect of impurities in graphene optical responses. Increase in the Fermi energy leads to an increase in the electron density in the graphene sheet, thereby enhancing the electric dipole generated by LSP on the nanomesh edges. A larger electric dipole results in stronger coupling to the incident EM wave and therefore increase in the light absorption irrespective of electron mobility as can be seen in FIGS. 5a-5b. Comparison between FIGS. 5a and 5b proves that the lower carrier mobility not only leads to a decrease in the plasmon lifetime, but also causes the merging of different plasmonic modes and broader asymmetric line-shape as predicted in FIGS. 2a-2d. The CDA model is employed to predict the spectral shift with Fermi level. As seen from FIGS. 5c and 5d (diagrams 110, 115), there is a good agreement between CDA predictions, experimental measurements, and analytical graphene plasmon frequency $\omega_p \propto \sqrt{E_F} \propto n^{1/4}$ [39] (detail CDA derivation is in SI).

Conclusion

Applicants have demonstrated for the first time that the direct excitation of cavity-coupled plasmon enhances the optical absorption in mono-layer graphene theoretically to around 60% and experimentally measured 45%, due to the strong coupling between LSP and optical cavity modes. Applicants have shown experimentally and theoretically that the carrier mobilty of the graphene, which is influenced by the defect density, determines the enhanced absorption bandwidth and line-shape. Further electronic tunability allows dynamic frequency tunable response. Such voltage tunable high absorption in mono-layer graphene will enable development of various practical graphene based optoelectronic devices like detectors, lasers, modulators etc.

Methods

Graphene growth: The graphene sheet is grown on a 25 µm thick copper foil in an oven composed of a molten silica tube heated in a split tube furnace. The molten silica tube and copper foil are loaded inside the furnace, evacuated, back filled with hydrogen, and heated up to 1000° C. while keeping a 50 sccm H$_2$ stream. The subsequent steps include reinstating the copper foil at 1000° C. for 30 minutes, inserting 80 sccm of CH$_4$ for 30 minutes. Then the furnace is cooled down to room temperature without gas feeding.

Cavity-couple nanoimprinted nanomesh graphene: An optically thick layer of Cr/Au (4 nm/200 nm) is deposited on a glass substrate as a back reflector using e-beam deposition. A photoresist (SU-8) layer is spin-coated on the gold back reflector to form an optical cavity, that is cured under UV lamp for 2 hours and baked on a hot plate for 1 hour at 95° C. in order to complete the cross-linking process. A thin layer (~20 nm) of Gold-Palladium (Au—Pd) is sputtered on the dielectric spacer which function as a gate electrode. A CVD-grown graphene sheet is transferred onto the Au—Pd layer using a PMMA transfer layer which is subsequently dissolved in Acetone. The square lattice hole pattern is fabricated following a simple large area nanoimprinting technique.[40,41] A poly dimethylsiloxane (PDMS) stamp is embossed against a thin photoresist (SU-8) layer that is spun coated on the graphene layer, followed by reactive ion etcher (RIE) in order to perforate the graphene layer. Low carrier mobility nanomesh graphene is prepared by rinsing the residual polymers (PMMA and SU-8) in acetone one time for a few seconds. In contrast, the high carrier mobility sample is prepared by repeating this process for more than ten times in order to reduce plolymer residues from the perforated graphene.

Electrostatic doping: A high capacitance ion gel film with refractive index of 1.3[42] is drop-casted on graphene in order to tune its Fermi energy to high values (~1 eV). Ion gel is a printable gate dielectric polymer[16,43] made by mixing ionic liquid ([EMIM][TFSI]) (Sigma-Aldrich, Inc.) with dry PS-PEO-PS (10-44-10 kg/mol) triblock copolymer (Polymer Source, Inc.) with ratio 1:0.04 in a dry solvent (dichloromethane) (Sigma-Aldrich, Inc.) and by stirring the mixture overnight. Then it is left for 48 hours inside high vacuum chamber (pressure<10$^{-6}$ torr) in order to evaporate the remaining solvent. The materials are dried in high vacuum for 24 hours then transferred to the glovebox for 4 days. The measured capacitance of this ion gel layer is C=1.2 µF/cm$^2$ and its absorbance in mid-IR spectrum is low. The Fermi energy of graphene is $E_F = \hbar v_F (\pi n)^{1/2}$, where $v_F \cong 10^6$ m/s is the Fermi velocity and n is the electron/hole density obtained by $$n_e = \frac{C \Delta V}{e},$$

where $\Delta V$ is gate voltage relative to charge neutral point (CNP). The gate is fabricated by depositing Cr/Au (3 nm/40 nm) on Si substrate. A copper wire is connected to the gate by applying silver paste on the side and back. The resulting substrate is flipped upside down and put on top of the ion gel.

Conductive AFM: After RIE and the polymer removal, conductive AFM was used to confirm the presence of a patterned graphene layer on the substrate. After patterning the graphene on copper foil following the same procedure and parameters used to pattern the graphene sheet on the SU-8 layer, conductive AFM (MultiMode, Atomic Force Microscope, Nanoscope III, Digital Instruments, Santa Barbara, Calif.) is employed to map of conductivity of the patterned graphene with nanoscale spatial resolution. Conductive (Au coated) cantilevers with spring constant k=0.06 N/m was used. Measurements are performed in contact mode and a full IV curve was collected at each pixel of the image. The 1 μm*1 μm map presented in FIGS. 3a-3d results from collecting 100*100 points. Image reconstruction was performed with Matlab.

Electromagnetic simulation: The theoretical simulations are done by finite-difference time-domain (FDTD) method using Lumerical FDTD (Lumerical Inc.) software. The analytical coupled dipole approximation (CDA) model is developed as outlined in the SI to study the behaviour of plasmons.

Optical measurements: The Raman spectrum of the grown graphene sheet is measured by WITec Renishaw RM 1000B Micro-Raman Spectrometer with an excitation laser wavelength of 514 nm and a 50× objective lens. The real and imaginary parts of the gold dielectric function used in simulations are taken from Palik[44]. The corresponding optical absorption measurements are performed with a microscope-coupled FTIR (Bruker Inc., Hyperion 1000-Vertex 80).

A more detailed description of the drawings now follows.

FIGS. 1a-1e Extraordinary absorption in cavity-coupled nanomesh graphene. FIG. 1a: Schematic of the (left) nanomesh and (right) cavity-coupled nanomesh graphene. FIG. 1b: (left) FDTD and CDA predicted absorption of the patterned nanomesh graphene. (right) FDTD prediction of absorption as a function of cavity thicknesses for the cavity-coupled case. The white solid and green dotted lines represent constructive and destructive cavity modes, respectively. FIG. 1c: Optical absorption of pristine, patterned and cavity coupled patterned graphene with cavity thickness of L1=1.6 μm, period=400 nm, diameter=330 nm, Ef=1.0 eV and μ=960 cm2/V·s. The first and second modes are marked by λ0 and λ1. FIG. 1d: The FDTD predicted real part and intensity of electric field distribution in z-direction for two plasmonic modes (λ0 and λ1). The white dotted circle line shows the graphene edges.

Figures 2A, 2B:
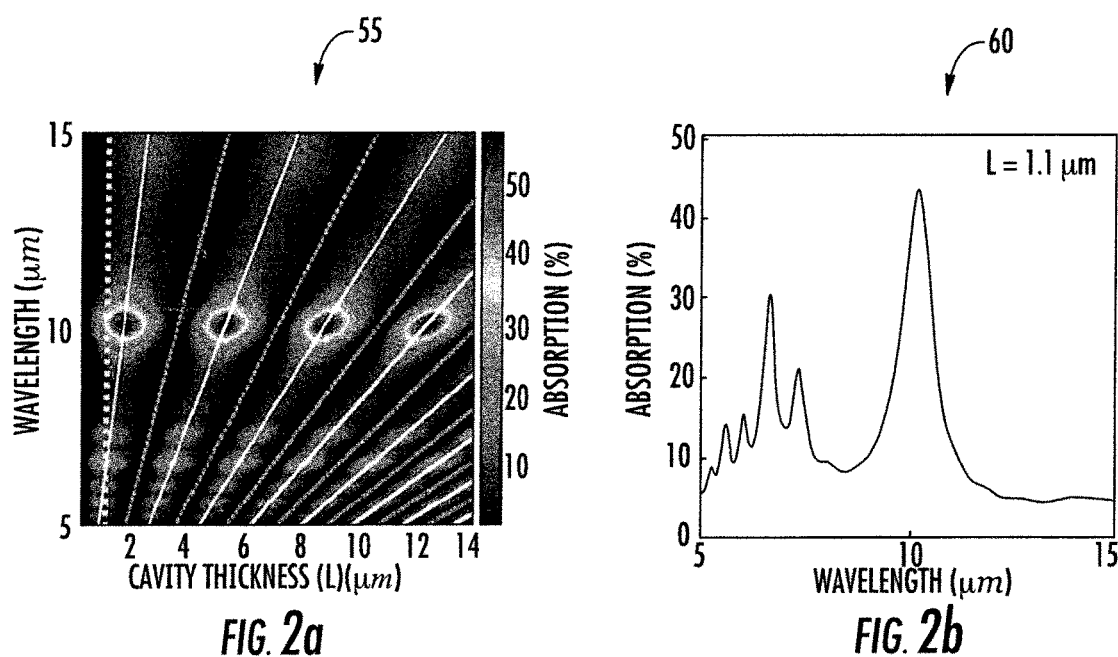
FIGS. 2a and 2b are diagrams of FDTD predicted cavity length (L) and wavelength dependent absorption, and wavelength dependent absorption at L=1.1 μm, respectively, at p=960 $cm^2/V \cdot s$, according to the present disclosure.
Figure 2C:
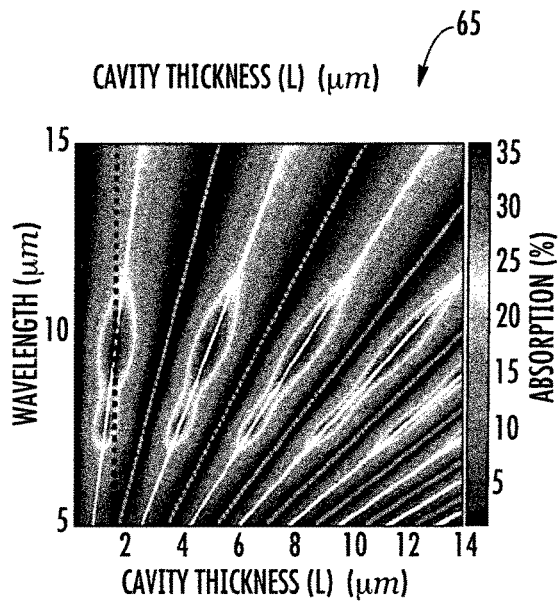
FIGS. 2c and 2d are the diagrams of FDTD predicted cavity length and wavelength dependent absorption, and wavelength dependent absorption at L=1.6 μm, respectively, at μ=250 $cm^2/V \cdot s$, according to the present disclosure
Figure 2D:
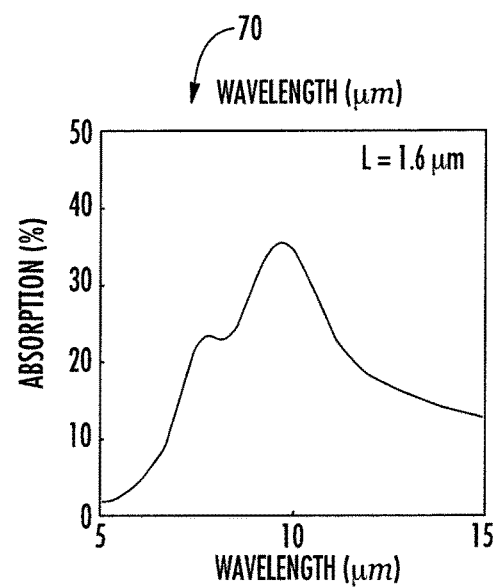

FIGS. 2a-2d: Effect of carrier mobility on absorption enhancement. FIG. 2a: FDTD predicted cavity length and wavelength dependent absorption for high and low mobility p=960 cm2/V·s and FIG. 2c: μ=250 cm2/V·s. The corresponding wavelength dependent absorption for two cavity thicknesses are shown in FIG. 2b and FIG. 2d respectively. Spectral broadening is observed for the low mobility case.

FIG. 3: Fabricated system. FIG. 3a: Schematic demonstration of the graphene plasmonic-cavity structure to excite surface plasmon for different Fermi energies. FIG. 3b: The Raman spectrum of grown pristine graphene. The presence of sharp and strong 2D peak proves mono-layer graphene. FIG. 3c: SEM image of the fabricated perforated graphene sheet on polymeric substrate (SU-8). FIG. 3d: Conductive AFM image of graphene nanomesh on copper foil. Change in in-plane conductivity distinctly shows the nanomesh formation on the mono-layer graphene.

FIGS. 4a-4b: Energy loss dispersion. FIG. 4a: The energy dispersion diagram. The colored two dimensional plot shows the evaluated loss function for the graphene with Ef=1.0 eV. ksp is the plasmon wavenumber associated with the second mode. The details can be found in the SI. ω0, ω1 and ω2 represent the LSPR, the resonance propagating plasmon frequency without and with plasmon-phonon interaction, respectively. The curved dotted white line is the plasmon dispersion relation of pristine suspended graphene. The shaded area indicates the Landau intra-band damping region. The constant pseudo-color diagram in the background marked by LSP is the loss function corresponds to the first mode which is LSP and independent of wavenumber. FIG. 4b: The experimental and theoretical prediction of the plasmon excitation on perforated graphene with period=400 nm, diameter=330 nm and μ=960 cm2/V·s coupled to an optical cavity with cavity thickness of 1.1 μm. The black solid, blue dotted and red disconnected line represent the experiment, FDTD predicted absorption spectrum without and with plasmon-phonon interaction, respectively. The coupling of surface plasmons of graphene and phonon polaritons of the substrate creates a new branch which is marked as SPPP. The unperturbed branch of graphene plasmons mode is GP. The localized surface plasmon is denoted by LSP.

FIGS. 5a-5d: Dynamically tunable response. Experimentally measured and theoretically predicted mobility dependent tunable absorption. Tunable absorption and absorption peak shift as a function of wavelength and Fermi energy (gate voltage) respectively for a (FIGS. 5a-5b) high (960 cm2/V·s) and (FIGS. 5c-5d) low (250 cm2/V·s) mobility mono-layer graphene. A cavity thickness of 1.1 μm and 1.6 μm were chosen for high and low mobility cases respectively.

In the following, exemplary mathematic models for peformance of perforated graphene is now discussed.

Supplementary Information

Calculation of Optical Extinction by Coupled Dipole Approximation

For analytical calculation of the optical extinction of the perforated graphene in the long wavelength limit, each element is considered as an electric dipole in the electrostatic limit with a specific polarizability $\alpha(\omega)$. Generally there are two different approaches to obtain $\alpha(\omega)$ for two dimensional perforated films. The first method defines the polarizability of the disk element as a Lorentzian function at the resonance frequency $$\alpha(\omega) = \frac{3c^3 \kappa_r}{2\omega_p^2} \frac{1}{\omega_p^2 - \omega^2 - \frac{i\kappa\omega^3}{\omega_p^2}}, \quad (1)$$

where $\omega_p$ is plasmon frequency of the single disk, $\kappa$ is the decay rate, and $\kappa_r$ is the radiative part of decay rate. The second procedure is based on the polarizability of a generalized ellipsoidal nanoparticle $$\alpha(\omega) = \varepsilon_0 V \frac{\varepsilon - \varepsilon_m}{\varepsilon + L_e(\varepsilon - \varepsilon_m)}, \quad (2)$$

where $\varepsilon$ and $\varepsilon_m$ are the dielectric functions of the conductive element and surrounding medium, respectively. V defines the volume, and the shape factor of the ellipsoid, $L_e$, is given by:

$$L_e = \frac{abc}{2} \int_0^\infty \frac{dq}{(a^2 + q)\{(q + a^2)(q + b^2)(q + c^2)\}^{\frac{1}{2}}}, \quad (3)$$

where a is the diameter of the ellipsoid along the light polarization direction, b and c are the diameters along other two dimensions. For the perforated graphene sheet a=b=d, where d is the hole diameter and c=t, where t is the thickness of graphene.

Derivation of the LSP frequency is possible by calculation of the total electric potential in presence of two dimensional nanostructure elements. The relation of the induced charge ($\mathfrak{S}$) and the current ($\mathcal{J}$) in the graphene sheet is given by the continuity equation $$\frac{\partial \mathfrak{S}}{\partial t} + \nabla \cdot \mathcal{J} = 0 \qquad (4)$$

Due to induction of the charge density by the incoming electromagnetic wave, it has exp(i$\omega$t) dependence and can be derived by means of $\mathcal{J}(r,\omega)$ $$\mathfrak{S}(r, \omega) = \frac{i}{\omega} \nabla \cdot \mathcal{J}(r, \omega) \qquad (5)$$

The induced current is related to the electric potential ($\phi$) by virtue of $\mathcal{J} = -\sigma \nabla \phi$, which yields the charge density $$\mathfrak{S}(r, \omega) = -\frac{i}{\omega} \nabla \cdot \sigma(r, \omega) \nabla \phi(r) \qquad (6)$$

The total electric potential in space is due to the combination of the radiation of the graphene nanostructure and the external electric field, i.e.

$$\phi(r) = \phi^{ext}(r) + \int_0^d \int_0^{2\pi} \frac{d^2 r' \mathfrak{S}(r', \omega)}{|r - r'|} \qquad (7)$$

Substitution of Eq. (6) in Eq. (7) gives $$\phi(r) = \phi^{ext}(r) - \frac{i}{\omega} \int_0^d \int_0^{2\pi} \frac{d^2 r' \nabla' \cdot \sigma(r', \omega) \nabla' \phi(r')}{|r - r'|} \qquad (8)$$

By assuming homogeneous doping of graphene, its conductivity does not depend on the position, and outside the graphene sheet the conductivity goes to zero. It means that $\sigma(r,\omega) = F(r)\sigma(\omega)$, where $f(r)=1/0$ for inside/outside the graphene sheet. By defining a dimensionless variable $$\mathfrak{R} = \frac{r}{d},$$

the electric potential is given by $$\phi(r) = \phi^{ext}(r) + \mathfrak{Y} \int_0^1 \int_0^{2\pi} \frac{d^2 \mathfrak{R}' \nabla' \cdot F(\mathfrak{R}') \nabla' \phi(\mathfrak{R}')}{|\mathfrak{R} - \mathfrak{R}'|} \qquad (9)$$

where $$\mathfrak{Y} = \frac{e^2 E_F}{\pi \hbar^2 \varepsilon_m d} \frac{1}{\omega(\omega + i\tau^{-1})} \qquad (10)$$

Eq. (9) introduces a self-consistent potential that in absence of external potential has real eigenvalues related to plasmonic modes. The LSP frequency is given by $$\omega_p = \frac{e}{\hbar} \sqrt{\frac{\mathfrak{X} E_F}{\pi \varepsilon_m d}} - \frac{i}{2\tau} \qquad (11)$$

where $\mathfrak{X}$ is the eigenvalue of Eq. (9) and can be derived by solving this eigensystem or by using the results from the FDTD simulation. The imaginary part of $\omega_p$ is responsible for the bandwidth of the absorption peak. In addition, eq. (11) can be applied for the graphene nanoribbon by replacing d (diameter) with w (nanoribbon width).

The lattice contribution S describes the near field and far field coupling of electric dipoles $$S = \sum_{j \neq i} \left[ \frac{(1 - ikr_{ij})(3\cos^2 \theta_{ij} - 1)e^{ikr_{ij}}}{r_{ij}^3} + \frac{k^2 \sin^2 \theta_{ij} e^{ikr_{ij}}}{r_{ij}} \right] \qquad (12)$$

where $r_{ij}$ is the distance between electric dipoles i and j, $\theta_{ij}$ is the angle between dipole j and $\vec{r}_{ij}$, and k defines the wavenumber. The optical reflection coefficient of the disk array can be calculated by using the polarizability and the lattice contribution $$r_{disk} = \frac{\pm i\mathfrak{E}}{\alpha^{-1} - S} \qquad (13)$$

where $$\mathfrak{E} = \frac{2\pi k}{A} \begin{cases} (\cos\vartheta)^{-1}, & s - \text{polarization} \\ \cos\vartheta, & p - \text{polarization} \end{cases} \qquad (14)$$

and $\theta$ is the incident angle, which is zero in our study, A is the area of the unit cell, and positive/negative sign stands for s/p polarization. The transmission coefficient of the disk array can be obtained through $t_{disk} = 1 + r_{disk}$.

The absorbance (A) of the disk array on the substrate can be derived by taking all of the reflected and transmitted electric fields at the interface of the pattern and the substrate into account $$A = 1 - |r_s + (1 + r_s)r_{disk}|^2 - \text{Re}\left(\sqrt{\frac{\varepsilon_2}{\varepsilon_1}}\right) |t_s|^2 |1 + r_{disk}|^2 \qquad (15)$$

where $\varepsilon_1$ and $\varepsilon_2$ are the dielectric functions of the surrounding media, and $r_s/t_s$ denote the reflection/transmission coefficient of the substrate $$r_s = \frac{\sqrt{\varepsilon_2} - \sqrt{\varepsilon_1}}{\sqrt{\varepsilon_2} + \sqrt{\varepsilon_1}} \qquad (16)$$

and $$t_s = \frac{2\sqrt{\varepsilon_1}}{\sqrt{\varepsilon_2} + \sqrt{\varepsilon_1}} \qquad (17)$$

Substitution of the real part of Eq. (11) into Eq. (1) with $\hbar\kappa = 12 \times 10^{-3}$ eV and $\hbar\kappa_r = 32.25 \times 10^{-5}$ eV, gives the polarizability of a single disk. The reflection coefficient of the disk array is evaluated by inserting the disk polarizabilities in Eq. (1) and Eq. (2) into Eq. (13). Then Eq. (15) provides the two analytical absorbances. This result in diagram 120 of FIG. 6*a* proves that the first mode corresponds to the hole-array LSP, lattice.

Analysis of the Different Plasmonic Modes

Figure 6A:
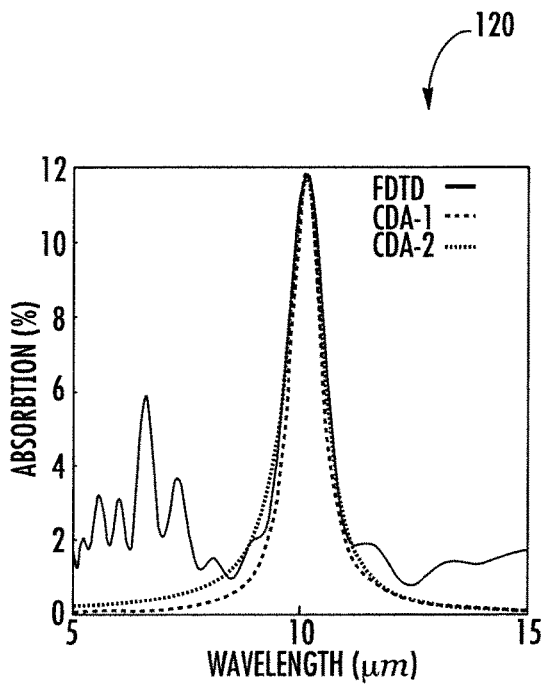
FIGS. 6a-6d are diagrams of light absorption of patterned graphene, and real part and intensity of electric field distribution in z direction derived from FDTD for different plasmonic modes, according to the present disclosure.
Figure 6B:
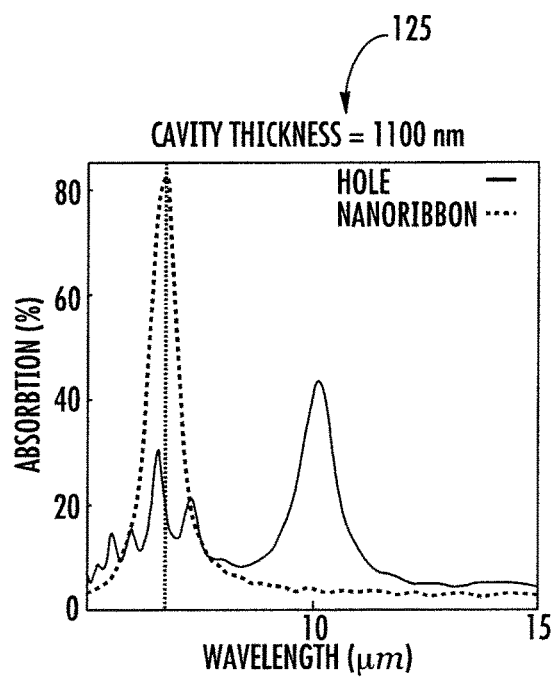
Figure 6C:
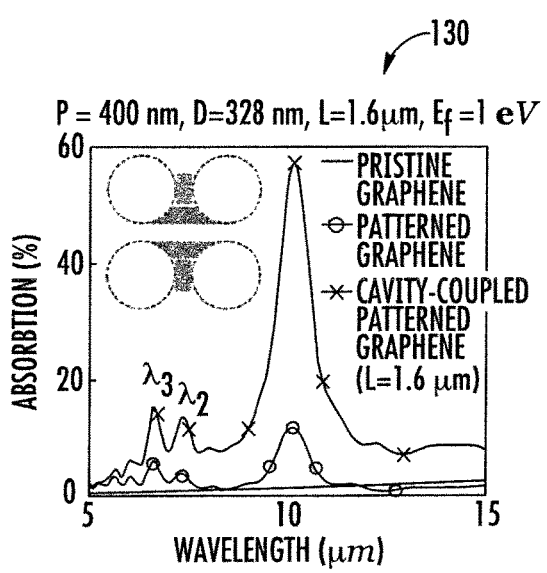
Figure 6D:
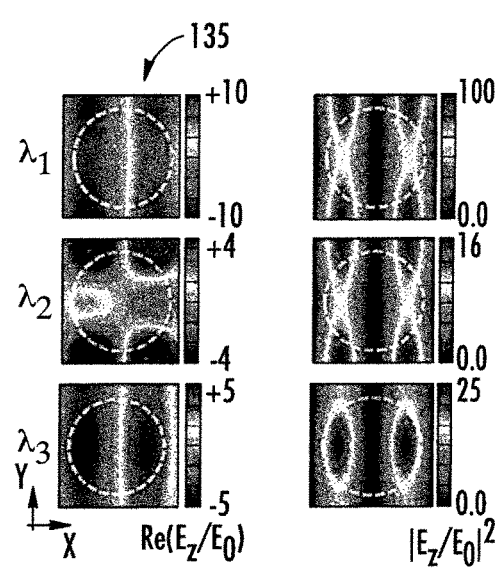

FIGS. 6*a*-6*d* are diagrams of analysis of two prominent peaks. FIG. 6*a*: The light absorption of patterned graphene with the carrier mobility of 960 cm$^2$/V·s, period=400 nm and diameter=330 nm without optical cavity obtained by FDTD and CDA approaches with different polarizabilities. FIG. 6*b*: The light absorption of cavity-coupled patterned graphene and graphene nanoribbon with width=70 nm. The dashed blue line shows the location of these two peaks are same. Optical absorption of pristine, patterned and cavity coupled patterned graphene with cavity thickness of $L_1$, Period=400 nm, Diameter=330 nm, $E_f$=1.0 eV and µ=960 cm$^2$/V·s. The first, second and third modes are shown by $\lambda_1$, $\lambda_2$ and $\lambda_3$, respectively. The inset image shows different regions which are responsible for those modes. FIG. 6*d*: The real part and intensity of electric field distribution in z direction derived from FDTD for different plasmonic modes. The white circle line shows the graphene edges.

According to FDTD results, the plasmon frequency of a graphene nanoribbon array with period=400 nm and width=70 nm, which is equal to the edge-edge distance of the holes, is equal to the resonance frequency of the third mode, as seen from diagram 125 of FIG. 6*b*. FIG. 6*c* (diagram 130) demonstrates three prominent absorption peaks appear due to exciting surface plasmons. The first mode labeled by $\lambda_1$. The red colored area has a much larger average width than the green colored area, and thus in accordance with Eq. (11) the plasmon resonance wavelength corresponding to the red colored area should be longer. Moreover, this mode is similar in shape with the mode of a square lattice of graphene nanodisks. The second mode ($\lambda_2$) coincides with the green region, which looks like the surface plasmon mode of a graphene nanoribbon. The plasmon resonance wavelength of an array of graphene nanoribbons with same width (70 nm) and period (400 nm) corresponds to the second peak. The nanoribbon array has a larger effective cross section to interact with the EM wave than the green region of the perforated sheet. That is why to the nanoribbon has a greater absorbance of 85%. The third mode ($\lambda_3$) exhibits an electric field distribution that changes sign back and forth in y direction, as shown in diagram 135 of FIG. 6*d*. The dipole strength of the mode $\lambda_1$ is substantially larger (i.e. >10%) than the modes $\lambda_2$ and $\lambda_3$ due to the larger cross section, which provides a higher electron density for the absorbance. According to FIGS. 1*c*-1*d* of the main manuscript, different modes can be intensified by choosing the appropriate cavity thickness, which provides another degree of tunability for this architecture. The different modes at lower wavelengths emerge because of diffraction of surface EM waves. For graphene in an asymmetric dielectric medium, the plasmon wavenumber ($k_p$) can be calculated by means of $$\frac{\varepsilon_1}{q_{z1}} + \frac{\varepsilon_2}{q_{z2}} + 2\sigma^{intra}(\omega) = 0 \quad (18)$$

where $\varepsilon_1$ and $\varepsilon_2$ are dielectric functions of adjacent environments, $q_{z1,2}=\sqrt{\varepsilon_{1,2}-(k_p/k)^2}$ is the wavenumber of incident EM wave. The diffraction orders correspond to the solutions of Eq. (18) which leads to appearing different peaks at lower wavelengths.

Plasmonic structures can be used to enhance the spontaneous emission rate due to wavelength confinement and amplification of the light-matter interaction. The enhancement of the spontaneous emission rate is determined by Q/V$_{eff}$ where Q is the quality factor given by the ratio of resonance frequency and peak bandwidth ($\omega_p/\lambda\omega$). The mode volume, derived via the EM field distribution, divided by the free space mode volume ($\lambda_0^3$) is equal to the effective mode volume V$_{eff}$. The calculated spontaneous emission enhancement for various modes and Fermi energies ranges from 10$^7$ to 10$^8$, which constitutes a 3 orders of magnitude increase relative to the simple metal plasmonic structure owing to the atomic thickness, the small loss of graphene, and the optical cavity.

Absorption of Substrate and Superstrate

FIG. 7*a* is a diagram of doping of graphene sheet by using ion gel as a dielectric for the capacitor. Charge neutrality point (CNP) is shown in the image. In FIG. 7*b*, the experimental result for the light absorption of the compound of SU-8 and ion gel.

The ion gel is used as dielectric to fabricate a capacitor for doping graphene electrostatically. The absorption of the compound of ion gel and SU-8 is shown in FIG. 7*b* (diagram 145), and the resistance is shown in diagram 140 of FIG. 7*a*. This compound has an absorption peak at the frequency $\omega \approx 36.2$ THz with bandwidth $\lambda\omega \approx 10$ THz, which is due to the excitation of longitudinal optical phonons. At higher wavelengths the absorption is around 50%, which is saturated for graphene absorbance larger than 50%. To obtain the pure light absorption by nanomesh graphene, the total absorption is normalized by the absorption of this compound.

Figure 9B:
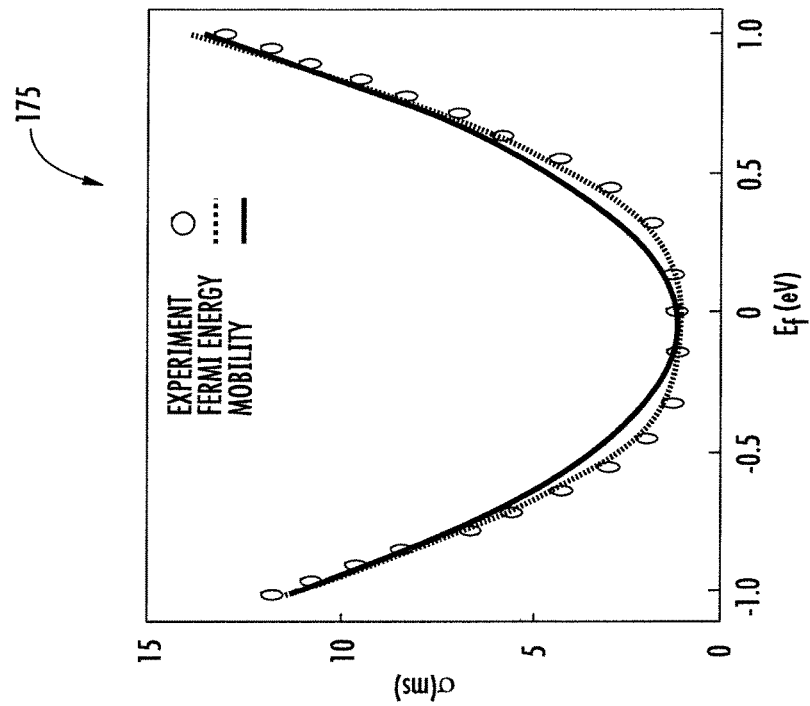
FIGS. 9a-9b are diagrams of electrical conductivity of graphene for different types of samples, according to the present disclosure.
Figure 9A:
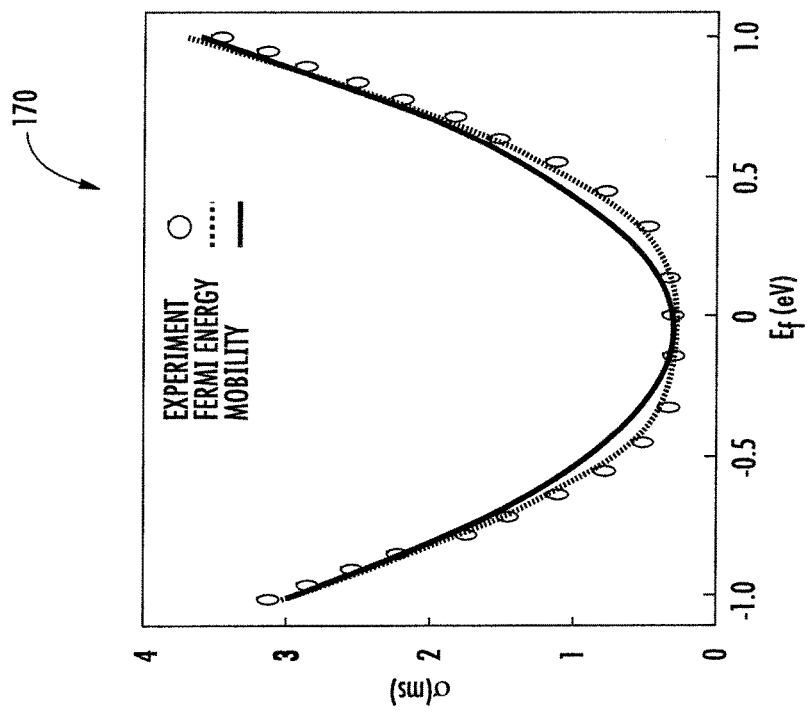

FIGS. 9*a*-9*b* are diagrams of electrical conductivity of graphene for different types of samples. Comparison of experimental results and analytical equations indicates µ=250 cm$^2$/V·s and µ=960 cm$^2$/V·s, respectively and the amount of Fermi energies correspond to different applied gate voltages.

The measured capacitance of the ion gel layer is C=2.4 µF/cm$^2$ and its absorption in mid-IR spectrum is low. The Fermi energy of graphene is $E_F=\hbar v_F(\pi n)^{1/2}$, where $v_F \cong 10^6$ m/s is the Fermi velocity and n is the electron/hole density obtained by $n_e=C\lambda V/$, where $\Delta V$ is gate voltage relative to charge neutral point (CNP). The reported Fermi eneries are calculated based on this relation. To prove the corresponding Fermi energies experimentally, the conductivity of graphene sheet is calcualed based on $\sigma(E_F)=\sigma_{min}(1+E_F^4/\Delta^4)^{1/2}$, where $\sigma_{min}$ is the minimum conductvity and $\Delta$ is the disorder strength parameter. As shown in diagrams 170, 175 of FIGS. 9*a*-9*b*, by fitting this conductivity to the experimental data (red dotted line), $\sigma_{min}$=0.289/0.371 ms and $\Delta$=297 meV/177 meV for FIGS. 9*a*-9*b*, respectively. The relation between conductivity and mobility is $\sigma$=neµ, where µ is the carrier mobility of graphene. Fitting this equation (green solid line) to the experimental results in FIGS. 9*a*-9*b* illustrates µ=250/960 cm$^2$/V·s for FIGS. 9*a*-9*b*, respectively. Positive and negative gate voltages correspond to n-doped and p-doped graphene, with a minimum conductivity occurring at the charge neutral point (CNP). According to these diagrams, the graphene sheet is doped a little bit during growth and transfer (0.05 eV).

Electrostatic Tuning of Absorption

Figure 8A:
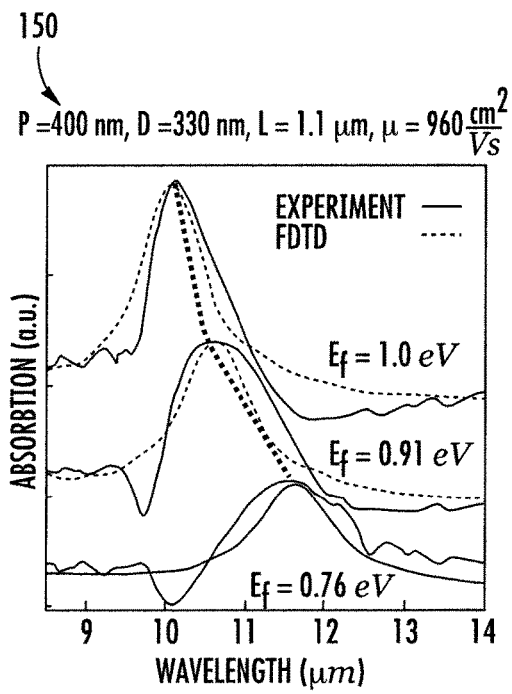
FIGS. 8a-8d are diagrams of experimental and theoretical plasmon excitation for different Fermi energies achieved by tuning the gate voltage, according to the present disclosure.
Figure 8B:
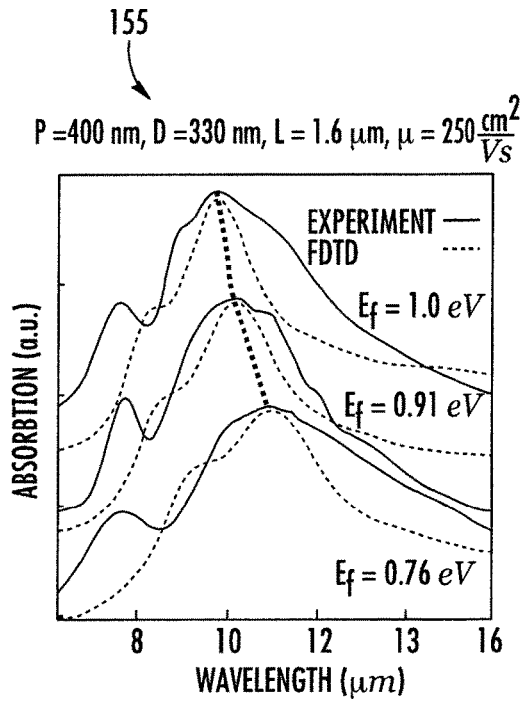
Figure 8C:
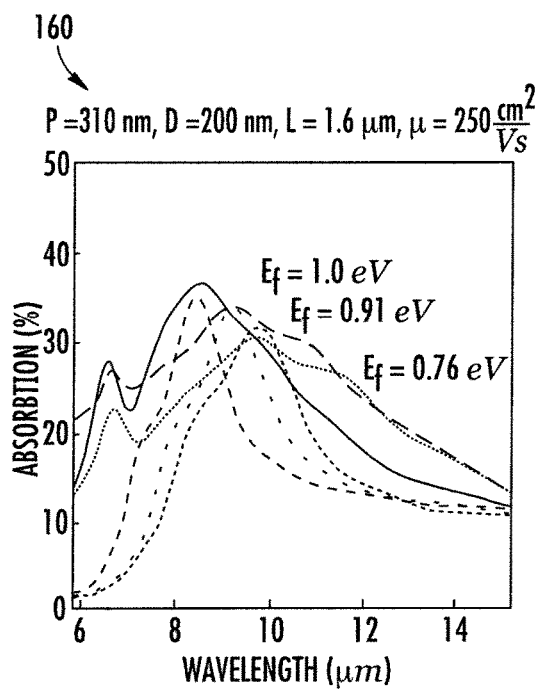
Figure 8D:
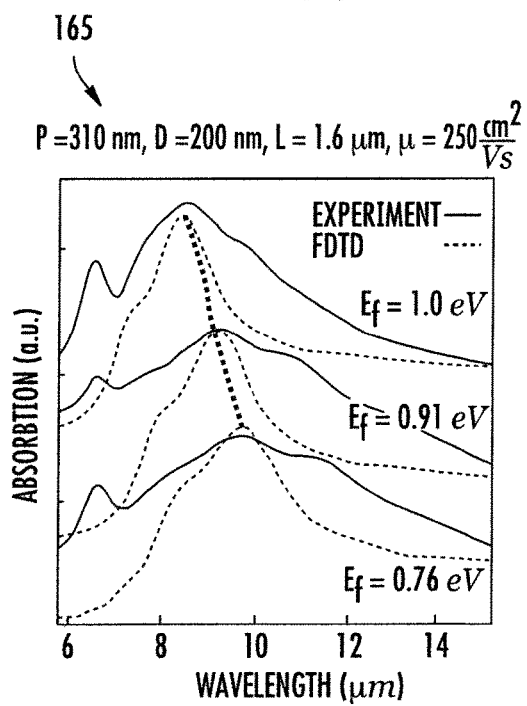

FIGS. 8*a*-8*d* are diagrams of experimental and theoretical plasmon excitation for different Fermi energies achieved by tuning the gate voltage. FIG. 8*a*: The first plasmonic mode of the cavity-coupled patterned graphene with the carrier mobility of 960 cm$^2$/V·s, period=400 nm, diameter=330 nm and cavity thickness=1.1 µm. The green dotted line shows the electronic tunability of the plasmon peaks. FIG. 8*b*: The electronic tuning of cavity-coupled patterned graphene with the carrier mobility of 250 cm$^2$/V·s, period=400 nm, diameter=330 nm and cavity thickness=1.6 µm. FIGS. 8*c*-8*d*: The electronic tuning of cavity-coupled patterned graphene with the carrier mobility of 250 cm$^2$/V·s, period=310 nm, diameter=200 nm and cavity thickness=1.6 µm.

According to Eq. (11), increasing the Fermi energy leads to blue shift of the resonance frequency, which are related to the graphene nanomesh with mobility µ=960 cm$^2$/(V·s) and µ=250 cm$^2$/(V·s), respectively. Another graphene sample with 250 cm$^2$/(V·s) mobility is perforated with 310 nm period and 200 nm diameter. This structure excites the LSP at the frequencies larger than that of the sample with 400 nm period and 330 nm diameter, which demonstrates another way for tuning the resonance frequency. Moreover, the plasmon frequency of this new structure is tunable by changing the Fermi energy. The constant peaks at lower wavelengths confirm the presence of the polymer residual. These results are shown in diagrams 150, 155, 160, 165 of FIGS. 8*a*-8*d*.

Calculating Loss Function and Effective Refractive Index of Graphene in Presence of Substrate In the random-phase approximation (RPA), for high frequencies the complex graphene conductivity is given by $$\sigma(\omega) = \frac{e^2\omega}{i\pi\hbar}\left[\int_{-\infty}^{+\infty}d\varepsilon\frac{|\varepsilon|}{\omega(\omega+i\tau^{-1})}\frac{dn_F(\varepsilon)}{d\varepsilon} - \int_{-\infty}^{+\infty}d\varepsilon\frac{n_F(-\varepsilon)-n_F(\varepsilon)}{(\omega+i\delta)^2-4\varepsilon^2}\right] \quad (19)$$

where $\delta \to 0$ is the infinitesimal parameter that is used to bypass the poles of the integral. The first and second terms correspond to the intraband electron-photon scattering processes and direct electron interband transitions, respectively. By taking the first integral, the intraband scattering is similar to the Drude conductivity $$\sigma^{intra}(\omega) = i\frac{2e^2k_BT}{\pi\hbar^2(\omega+i\tau^{-1})}\ln\left(2\cosh\frac{E_F}{2k_BT}\right) \quad (20)$$

where $k_B$ is the Boltzmann constant and T is the temperature. At low temperatures $k_BT \ll E_F$, the graphene conductivity follows the Drude model $$\sigma^{intra}(\omega) \approx i\frac{e^2E_F}{\pi\hbar^2(\omega+i\tau^{-1})} \quad (21)$$

According to the charge conservation law, the relation of the bulk current $J_V$ and the surface current $J_S$ for a material is given by $$\iint J_S ds = \iiint J_V dV \quad (22)$$

which means the relation of two and three dimensional conductivity is defined by $$\sigma_{3D} = \frac{\sigma_{2D}}{t} \quad (23)$$

where t describes the thickness of the material. The dielectric function of graphene can be obtained via its AC conductivity by means of $$\varepsilon(\omega) = \varepsilon_g + \frac{i\sigma_{3D}}{\varepsilon_0\omega} \quad (24)$$

where $\varepsilon_g$=2.5 is the dielectric constant of graphite.

Substituting Eq. (23) into Eq. (24) gives the in-plane dielectric function of graphene, i.e.

$$\varepsilon(\omega) = \varepsilon_g + \frac{i\sigma^{intra}}{\varepsilon_0\omega t} = \varepsilon_g - \frac{e^2E_F}{\pi\hbar^2\varepsilon_0\omega(\omega+i\tau^{-1})t} \quad (25)$$

whereas the surface-normal component is $\varepsilon_z$=2.5.

The Dynamical Polarization $$P(q, i\omega_n) = -\frac{1}{A}\int_0^\beta d\tau e^{i\omega_n\tau}\langle T\rho_q(\tau)\rho_{-q}(0)\rangle \quad (26)$$

determines several important quantities such as effective electron-electron interaction, plasmon and phonon spectra, and Friedel oscillations.

$$\omega_n = \frac{2\pi n}{\beta}$$

are Matsubara frequencies, $\rho_q$ is the density operator in q-space and A denotes the area. This quantity is calculated in the canonical ensemble for both of the sub-lattice density operators ($\rho=\rho_a+\rho_b$). Eqs. (26)-(33) have been used to derive the dynamical polarization. The dynamical polarization up to the first order electron-electron interaction in the long wavelength limit is $$P^{(1)}(q, i\omega_n) = \quad (27)$$

$$\frac{g_s g_v}{4\pi^2}\int d^2k \sum_{s,\acute{s}=\pm} f^{s\acute{s}}(k,q)\frac{n_F(E^s(k))-n_F(E^{\acute{s}}(|k+q|))}{E^s(k)-E^{\acute{s}}(|k+q|)+i\hbar\omega_n}$$

where $g_s=g_v=2$ are the spin and valley degeneracy, $n_F$ is the Fermi distribution and $E^s(k)=s\hbar v_F k-E_F$ is the graphene energy. The band-overlap of wavefunctions, $f^{s\acute{s}}(k,q)$, is a specific property of graphene $$f^{s\acute{s}}(k,q) = \frac{1}{2}\left(1+s\acute{s}\frac{k+q\cos\varphi}{|k+q|}\right) \quad (28)$$

where $\varphi$ signifies the angle between k and q.

Integration over $\varphi$ and k gives the retarded polarization or charge-charge correlation function $$P^{(1)}(q,\omega) = P_0^{(1)}(q,\omega) + \Delta P^{(1)}(q,\omega) \quad (29)$$

where

-continued $$P_0^{(1)}(q,\omega) = -i\pi \frac{\mathfrak{F}(q,\omega)}{\hbar^2 v_F^2} \quad (30)$$

and $$\Delta P^{(1)}(q,\omega) = -\frac{gE_F}{2\pi\hbar^2 v_F^2} + \frac{\mathfrak{F}(q,\omega)}{\hbar^2 v_F^2} \quad (31)$$

$$\left\{\mathfrak{G}\left(\frac{\hbar\omega + 2E_F}{\hbar v_F q}\right) - \Theta\left(\frac{2E_F - \hbar\omega}{\hbar v_F q} - 1\right) \times \left[\mathfrak{G}\left(\frac{2E_F - \hbar\omega}{\hbar v_F q}\right) - i\pi\right] - \Theta\left(\frac{\hbar\omega - 2E_F}{\hbar v_F q} + 1\right)\mathfrak{G}\left(\frac{\hbar\omega - 2E_F}{\hbar v_F q}\right)\right\}$$

Two functions $\mathfrak{F}(q,\omega)$ and $\mathfrak{G}(x)$ are defined as $$\mathfrak{F}(q,\omega) = \frac{g}{16\pi} \frac{\hbar v_F^2 q^2}{\sqrt{\omega^2 - v_F^2 q^2}} \quad \text{and} \quad (32)$$

$$\mathfrak{G}(x) = x\sqrt{x^2 - 1} - \ln(x + \sqrt{x^2 - 1}) \quad (33)$$

where $g = g_s g_v = 4$.

For $\omega > qv_F$ and in the long wavelength limit $$q \to 0, \, x = \left|\frac{\hbar\omega \pm 2E_F}{\hbar v_F q}\right| \gg 1,$$

so $x^2 - 1 \approx x^2$ and $\mathfrak{G}(x) \approx x^2 - 2\ln(x)$. We derive here the dynamical polarization (Eq. (38)) and the effective dielectric of graphene on the substrate (Eq. (51)) in these regimes. The expansion of $\mathfrak{F}(q,\omega)$ gives $$\mathfrak{F}(q,\omega) = \frac{g}{16\pi} \frac{\hbar v_F^2 q^2}{\omega}\left(1 - \frac{v_F^2 q^2}{\omega^2}\right)^{1/2} \approx \frac{g}{16\pi} \frac{\hbar v_F^2 q^2}{\omega}\left(1 + \frac{v_F^2 q^2}{\omega^2}\right) \quad (34)$$

In this condition and for intraband transition ($\hbar\omega < 2\mu$)

$$\mathfrak{G}\left(\frac{\hbar\omega + 2E_F}{\hbar v_F q}\right) - \mathfrak{G}\left(\frac{2E_F - \hbar\omega}{\hbar v_F q}\right) = \frac{8\hbar\omega E_F}{\hbar^2 v_F^2 q^2} + 2\ln\left(\left|\frac{2E_F - \hbar\omega}{2E_F + \hbar\omega}\right|\right) \quad (35)$$

As a result, $\Delta P^{(1)}(q,\omega)$ reduces to $$\Delta P^{(1)}(q,\omega) = \quad (36)$$

$$-\frac{gE_F}{2\pi\hbar^2 v_F^2} + \frac{\mathfrak{F}(q,\omega)}{\hbar^2 v_F^2}\left\{\frac{8\hbar\omega E_F}{\hbar^2 v_F^2 q^2} + 2\ln\left(\left|\frac{2E_F - \hbar\omega}{2E_F + \hbar\omega}\right|\right) + i\pi\right\} =$$

$$\frac{gq^2}{8\pi\hbar\omega}\left\{\frac{2E_F}{\hbar\omega} + \frac{1}{2}\ln\left(\left|\frac{2E_F - \hbar\omega}{2E_F + \hbar\omega}\right|\right) + \frac{i\pi}{2}\right\}$$

If $2E_F \gg \hbar\omega$ $$\Delta P^{(1)}(q,\omega) = \frac{gq^2}{8\pi\hbar\omega}\left[\frac{2E_F}{\hbar\omega} + \frac{i\pi}{2}\right] \quad (37)$$

By taking the decay rate $\omega \to \omega + i\tau^{-1}$ into account and substituting Eq. (30) into Eq. (29), the dynamical polarization reduces to $$P^{(1)}(q,\omega) \approx \frac{E_F q^2}{\pi\hbar^2(\omega + i\tau^{-1})^2} \quad (38)$$

The electron life time ($\tau$) can be derived by considering the impurity, electron-phonon interaction and the scattering related to nanostructure edges $$\tau = \tau_{DC}^{-1} + \tau_{edge}^{-1} + \tau_{e\text{-}ph}^{-1} \quad (39)$$

where $\tau_{DC} = 95$ fs is the lifetime measured from Drude response of the pristine graphene. It can be evaluated via the measured DC mobility ($\mu$) of the graphene sample through $$\tau_{DC} = \frac{\mu\hbar}{eV_F}\sqrt{\pi n} \quad (40)$$

where $V_F \sim 10^6$ m/s is the Fermi velocity and $n = (E_F/\hbar V_F)^2/\pi$ is the charge carrier density.

$$\tau_{edge} \approx \frac{3 \times 10^6}{w - w_0}$$

is due to the scattering from the nanostructure edges, and $\tau_{e\text{-}ph} = \hbar/2\Im(\Sigma_{e\text{-}ph})$ is related to the scattering because of coupling of electrons and phonons $$\Im(\tau_{e\text{-}ph}) = \gamma|\hbar\omega - \text{sgn}(\hbar\omega - E_F)\hbar\omega_{oph}| \quad (41)$$

where $\Sigma_{e\text{-}ph}$ is the electron self-energy, $\gamma = 18.3 \times 10^{-3}$ is a dimensionless constant describing the electron-phonon coupling coefficient, and $\hbar\omega_{oph} \approx 0.2$ eV is the graphene optical phonon energy.

In the presence of the optical phonons, the effective dielectric function can be calculated via RPA expansion of the dielectric function $$\varepsilon^{RPA}(q,\omega) = \varepsilon_m - v_c(q)P^{(1)}(q,\omega) - \varepsilon_m\Sigma_l v_{sph,l}(q,\omega)P^{(1)}(q,\omega) - \varepsilon_m v_{op}(q,\omega)P_{jj}^{-1}(q,\omega) \quad (42)$$

where $$\varepsilon_m = \frac{\varepsilon_1 + \varepsilon_2}{2}$$

is the average of dielectric constants of graphene's environment. The second term represents the effective Coulomb interaction of electrons in graphene, and $$V_c = \frac{e^2}{2q\varepsilon_0}$$

is the direct Coulomb interaction. The third term is the effective dielectric function for different phonon modes (l) coming from electron-electron interaction mediated by substrate optical phonons, which couple to the electrons by means of the Fröhlich interaction, i.e.)

$$v_{sph,l}(q,\omega)|M_{sph}|^2 G_1^0(\omega) \quad (43)$$

where $|M_{sph}|^2$ is the scattering matrix element given by $$|M_{sph}|^2 = \frac{\pi e^2}{\varepsilon_0} \frac{e^{-2qz_0}}{q} \mathcal{F}^2 \quad (44)$$

where $z_0$ is the distance between the graphene and the substrate, and $\mathcal{F}^2$ denotes the Fröhlich coupling strength. The free phonon Green's function $G_1^0$ is defined as $$G_l^0(\omega) = \frac{2\omega_{sph,l}}{\hbar\left(\left(\omega + \frac{i\hbar}{\tau_{sph,l}}\right)^2 - \omega_{sph,l}^2\right)} \quad (45)$$

where $\omega_{sph}$ and $\tau_{sph}$ are the substrate phonon frequency and lifetime, respectively. The last term of Eq. (42) corresponds to graphene's optical phonon mediated electron-electron interaction $$\nu_{oph}(q,\omega) = |M_{op}|^2 G^o(\omega) \quad (46)$$

Here $|M_{oph}|^2$ defines the scattering matrix element $$|M_{oph}|^2 = \frac{\hbar g_0^2}{2\rho_m \omega_{op}} \quad (47)$$

where $g_0 = 7.7$ eV/A° is the coupling constant, $\rho_m$ is the mass density of graphene, and $\omega_{op}$ is the graphene optical phonon frequency. Similar to the substrate phonon case, $G^o(\omega)$ is the free phonon Green's function $$G^o(\omega) = \frac{2\omega_{op}}{\hbar\left(\left(\omega + \frac{i\hbar}{\tau_{oph}}\right)^2 - \omega_{oph}^2\right)} \quad (48)$$

where $\tau_{oph}$ is the graphene optical phonon lifetime. In Eq. (42), $P_{j,j}^1(q,\omega)$ is the current-current correlation function which is related to the retarded polarization by means of the charge continuity equation $$P_{j,j}^1(q,\omega) = \frac{\omega^2}{q^2} P^{(1)}(q,\omega) - \frac{v_F}{q^2} \langle [q \cdot \hat{J}_q, \hat{\rho}_{-q}] \rangle \quad (49)$$

where $\hat{J}_q$ is the single-particle current operator in q-space. Since the second term is purely real, the imaginary part of $P_{j,j}^1(q,\omega)$ can be calculated by evaluating imaginary part of the first term.

Collective oscillation of electron modes can be obtained by setting $\varepsilon^{RPA}(q,\omega)=0$. The extinction function is identified as $$Z = -\frac{\delta T}{T_0},$$

or for the plasmonic structure coupled to an optical cavity $$Z = -\frac{\delta R}{R_0},$$

where $\delta R = R - R_0$ and $R/R_0$ is the reflectance with/without plasmon excitation, which corresponds to the enhanced absorbance at resonance frequencies $$Z \sim -\Im\left(\frac{1}{\varepsilon^{RPA}}\right) \quad (50)$$

In the long wavelength regime, by substituting Eq. (38) and $v_c$ into Eq. (42), the second term on the right hand side is reduced to the Drude model dielectric function $$\varepsilon_{Drude} = -v_c(q)P^{(1)}(q,\omega) = -\frac{e^2 E_f q}{2\varepsilon_0 \pi \hbar^2(\omega + i\tau^{-1})^2} \quad (51)$$

According to Eq. (25), the in-plane momentum of the pristine graphene should be equal to $$q = \frac{2}{t}.$$

So, the effective dielectric function of graphene on the substrate is given by $$\varepsilon^{RPA}(q,\omega) = \varepsilon^{Drude} - \Sigma_m \Sigma_l \nu_{sph,l}(q,\omega)P^{(1)}(q,\omega) - \varepsilon_m \nu_{oph}(q,\omega)P_{j,j}^1(q,\omega) \quad (52)$$

In this dielectric function, the phonon terms, which are small relative to $\varepsilon^{Drude}$, perturb the original system. In order to include the electron-phonon coupling in the simulation and to predict the experimental results with higher accuracy, Eq. (52) has been used as the input data in the FDTD simulations to generate the red diagram of FIG. 4b in the main manuscript.

Referring now to FIG. 10, a diagram 180 is now described. The diagram 180 shows light absorption of cavity coupled patterned graphene with cavity thickness of L=1400 nm, Period=400 nm, Diameter=330 nm, $E_f$=1.0 eV and μ=960 cm$^2$/V·s for different auto shutoff mins.

Referring now to FIGS. 11*a*-11*b*, diagrams 185, 190 are now described. The diagrams 185, 190 show electrical conductivities of monolayer graphene sheets with different carrier mobilities. Experimental results and analytical calculations for FIG. 11*a* μ=250 cm$^2$/V·s and FIG. 11*b* μ=960 cm$^2$/V·s show the dependence of electrical conductivity on Fermi energy. The dotted line is the electrical conductivity by $\sigma(E_F) = \sigma_{min}(1 + E_F^4/\Delta^4)^{1/2}$ and the solid line demonstrates σ=ρeμ.

Figure 12A:
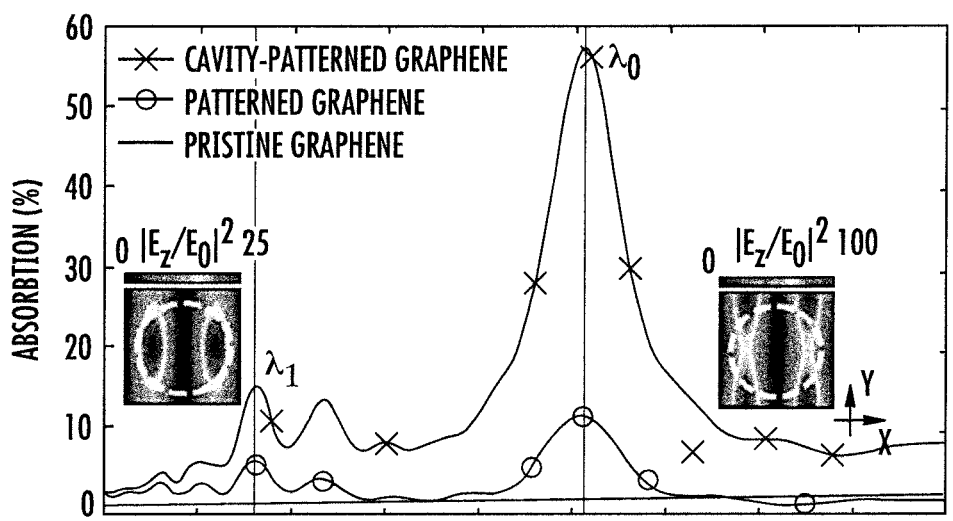
FIGS. 12a-12b are diagrams of simulated and experimental optical absorption spectra, respectively, according to the present disclosure.
Figure 12B:
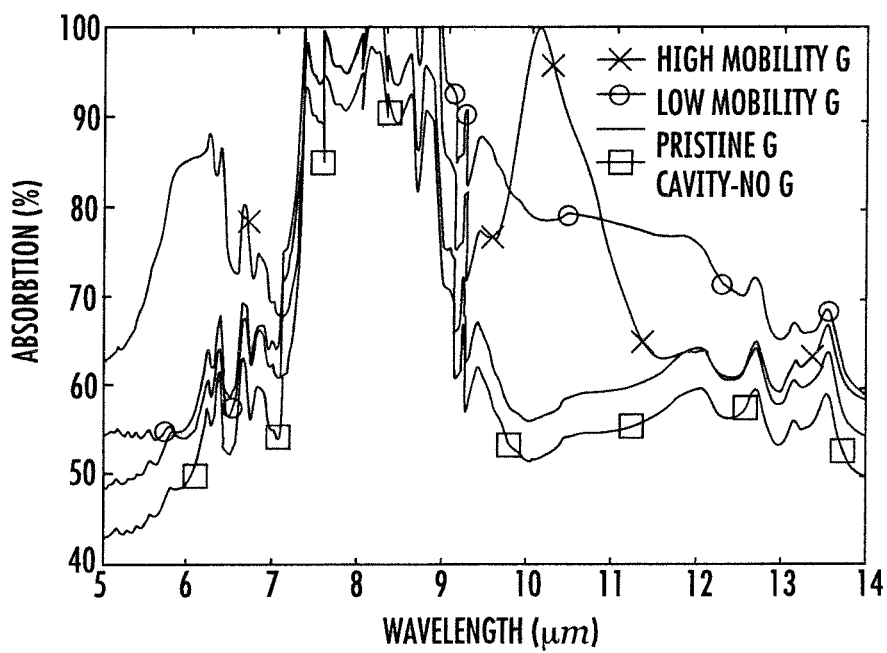

Referring now to FIGS. 12*a*-12*b*, diagrams 195, 200 are now described. The diagrams 195, 200 show, in FIG. 12*a*, optical absorption of pristine, patterned and cavity coupled patterned graphene with cavity thickness of $L_1$, Period=400 nm, Diameter=330 nm, $E_f$=1.0 eV and μ=960 cm$^2$/V·s. The first and modes are shown by $\lambda_0$ and $\lambda_1$, respectively. The inset images show the intensity of electric field distribution in z direction derived from FDTD for different plasmonic modes. The white circle line shows the graphene edges. In FIG. 12*b*, the experimental result for the light absorption of the whole structure without graphene (square marked line), and the total light absorption of doped patterned graphene and substrate/superstrate (x marked line: high mobility to circle marked line: low mobility), pristine graphene and substrate/superstrate (solid line) and bare pristine graphene (solid line).

Figure 13:
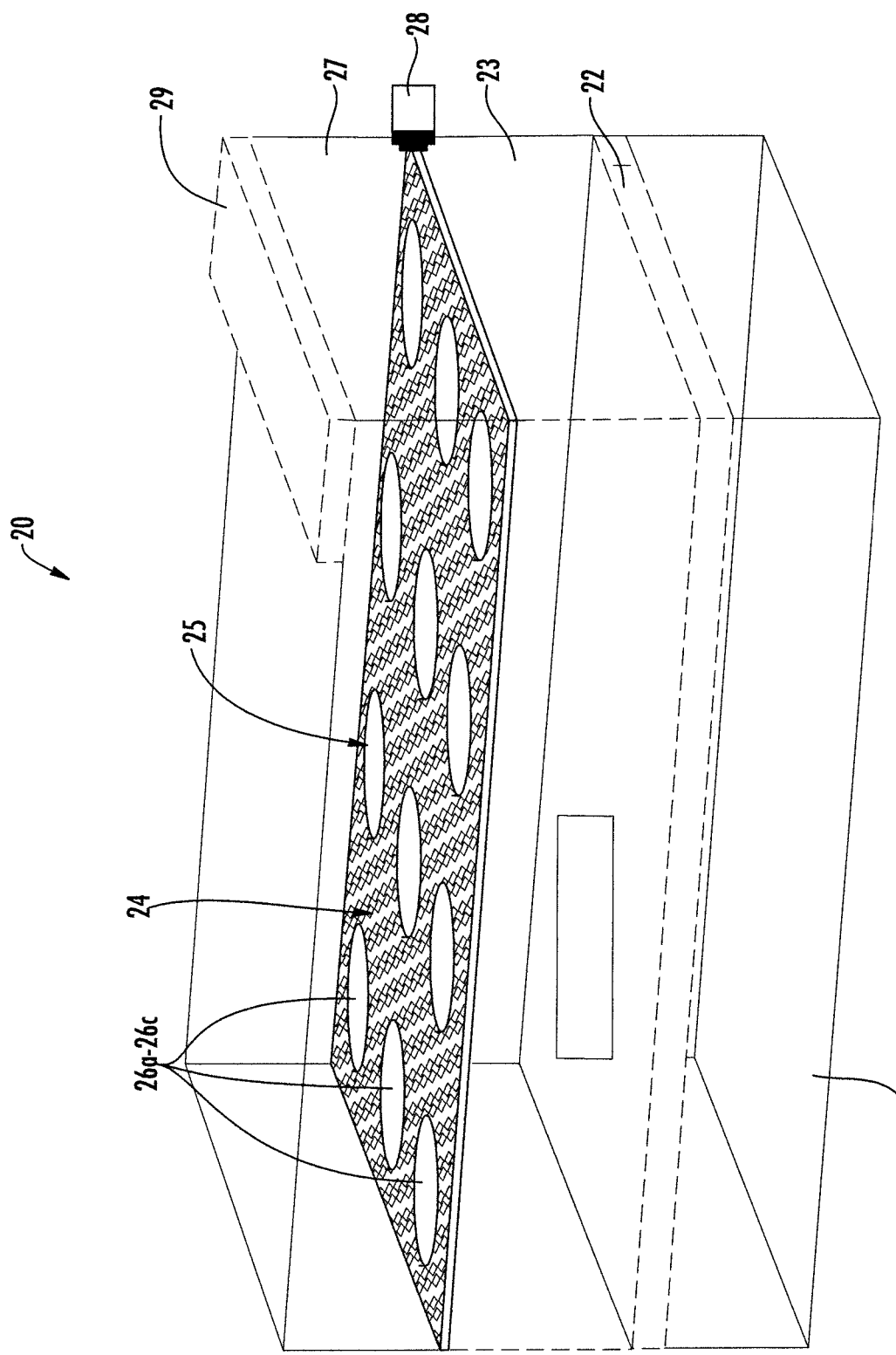
FIG. 13 is a schematic diagram of an optical detector device, according to the present disclosure.

Referring now to FIG. 13, an optical detector device 20 according to the present disclosure is now described. The optical detector device 20 illustratively includes a substrate 21 (e.g. glass), and a reflector layer 22 carried by the substrate. The optical detector device 20 illustratively includes a first dielectric layer 23 over the reflector layer 22, and a graphene layer 24 over the first dielectric layer and having a perforated pattern 25 therein.

The perforated pattern 25 illustratively includes a square array of openings 26a-26c. For example, in the illustrated embodiment, each of the openings 26a-26c is circle-shaped. In other embodiments (not show), the openings 26a-260 may have another shape, such as a square, an oval, or a triangle. The perforated pattern 25 is illustratively symmetrical about longitudinal and transverse axes. The first dielectric layer 23 may comprise one or more of an ion gel, a polymer material, and a SU-8 epoxy-based negative photoresist, for example. Also, in the illustrated embodiment, the graphene layer 24 includes a monolayer of graphene (i.e. a layer having a thickness of one molecule).

Also, the optical detector device 20 illustratively includes a second dielectric layer 27 over the graphene layer 24, a first electrically conductive contact 29 coupled to the second dielectric layer (e.g. polymer material), and a second electrically conductive contact 28 coupled to the graphene layer. The second dielectric layer 27 may comprise one or more of an ion gel, and a polymer material, for example.

In some embodiments, the first and second electrically conductive contacts 28, 29 each comprises one or more of aluminum, palladium, copper, gold, and silver. The reflector layer 22 may comprise gold material, for example. In some embodiments, the reflector layer 22 may comprise a gold backed mirror. The reflector layer 22 may have a thickness greater than a threshold thickness for optical opacity.

Another aspect is directed to a method for making an optical detector device 10. The method includes forming a reflector layer 22 carried by a substrate 21, forming a first dielectric layer 23 over the reflector layer, and forming a graphene layer 24 over the first dielectric layer and having a perforated pattern 25 therein.

Figure 14:
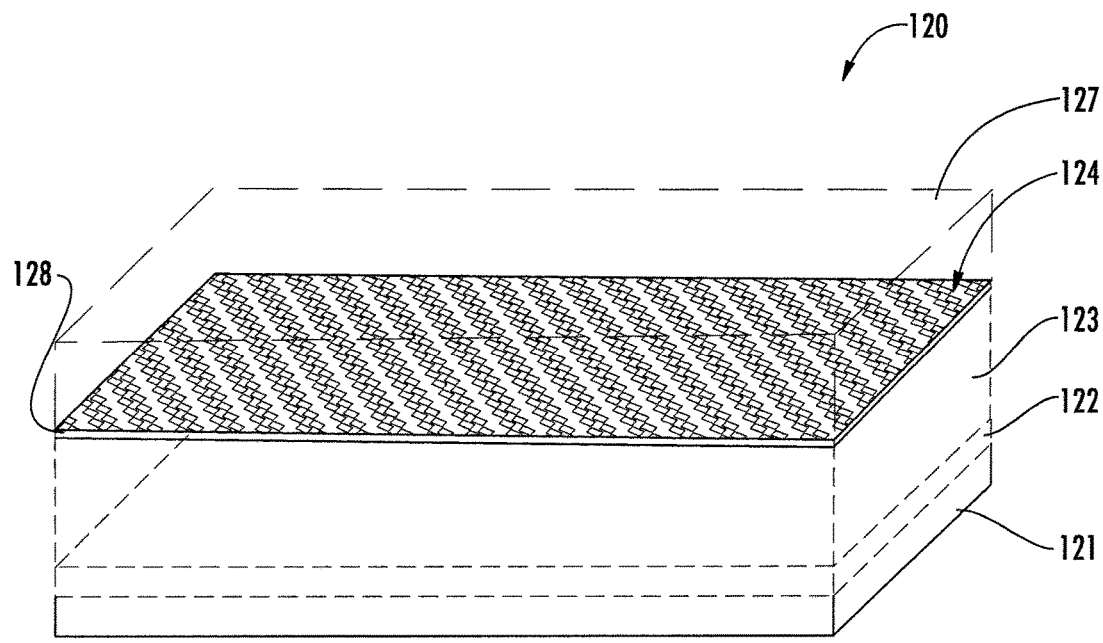
FIG. 14 is a schematic diagram of another embodiment of the optical detector device, according to the present disclosure.

Referring now additionally to FIG. 14, another embodiment of the optical detector device 120 is now described. In this embodiment of the optical detector device 120, those elements already discussed above with respect to FIG. 13 are incremented by 100 and most require no further discussion herein. This embodiment differs from the previous embodiment in that this optical detector device 120 illustratively includes an unpatterned graphene layer 124.

Figure 15:
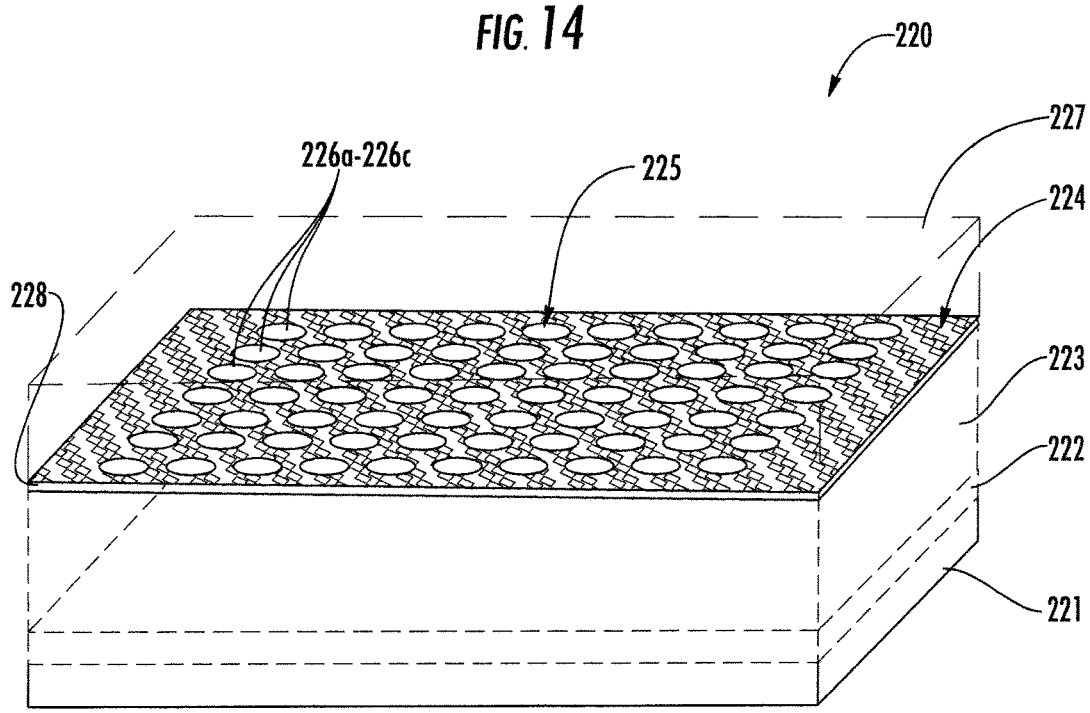
FIG. 15 is a schematic diagram of another embodiment of the optical detector device, according to the present disclosure.

Referring now additionally to FIG. 15, another embodiment of the optical detector device 220 is now described. In this embodiment of the optical detector device 220, those elements already discussed above with respect to FIG. 13 are incremented by 200 and most require no further discussion herein. This embodiment differs from the previous embodiment in that this optical detector device 220 illustratively includes the graphene layer 224 having a perforated pattern 225 with ten rows of seven openings 226a-226c.

In the following, some additional exemplary discussion now follows.
Design and Simulation Results An array of nanoholes on graphene conserves the continuity of graphene, and by coupling this perforated graphene to an optical cavity, we show that it is possible to achieve constructive interference between the incident and scattered electric fields, giving rise to strong enhancement of the absorption. Consequently, the strong light-matter interaction amplifies direct light absorption in graphene even in conditions of low carrier mobility, unlike other techniques where high carrier mobility is required for absorption enhancement. The system consists of a dielectric slab of thickness L and refractive index $n_d$=156 sandwiched between patterned graphene and an optically thick (200 nm) gold back reflector, as illustrated in FIG. 1d—right (inset). The patterned graphene is obtained by perforating a square array of holes with 330 nm diameter and 400 nm period. A simple embossing based nanoimprinting technique was followed to pattern the graphene sheet. The cavity supports transverse electromagnetic modes when the slab thickness satisfies the phase equation $L=m\lambda/4n_{eff}$, where $n_{eff}$ is the effective refractive index of the dielectric slab, $\Delta$ is the incident electromagnetic wavelength, and m=[1,2,3, . . . ] is the m-th order of the optical cavity mode. The $n_{eff}$ value, which includes the effect of patterned graphene is calculated by the effective medium approach. The finite-difference time domain (FDTD) simulations (with auto shutoff min of $10^{-8}$, simulation time of 5000 fs and meshing of 0.05 nm) reveal that for odd/even cavity modes excited with x-polarized light, the incident and reflected electric fields interfere constructively/destructively giving rise to a maximum/minimum value in the surface plasmon enhanced absorption for graphene with electron mobility of $\mu$=960 cm$^2$/V·s and Fermi energy of $E_F$=1.0 eV (FIG. 1d). In the case of destructive interference, the incident and reflected electric fields have a phase difference of n such that their interference results in zero net amplitude. The FDTD absorption spectrum (FIG. 1c) shows two distinct peaks at $\omega_0$ and $\omega_1$, which can be attributed to localized surface plasmon (LSP) and propagating surface plasmon (SPP) modes, respectively. This is evident from the corresponding real [Re($E_z$)] part and intensity ($|E_z|^2$) of the z-component of the electric field distribution for both plasmonic modes, as shown in FIG. 12a (inset). The nature of the plasmonic mode at $\omega_0$ is further confirmed to be a LSP because of the close correspondence between the FDTD and coupled dipole approximation (CDA) modelled absorption spectra of the patterned graphene without optical cavity (FIG. 1c). Due to the symmetrical square lattice pattern of the holes, the excitation of LSP is independent of light polarization for normal angle of incidence. The solid white and green dotted lines in the FDTD calculation in FIG. 1d show the analytical dispersions of the cavity modes as a function of wavelength and cavity thickness, which accurately depicts the origin of this extraordinary absorption arising from the temporal and spatial overlap between the LSP resonance and the cavity modes.

The FDTD simulation shows that a cavity length of L=1.6 μm, which satisfies the cavity resonance condition, needs to be chosen in order to achieve ~60% light absorption in patterned graphene at around λ=10 μm, giving rise to about a 30-fold absorption enhancement compared to pristine graphene. We use the optical cavity to strongly increase the absorption of the incident light by means of the enhancement of the electric field on the patterned graphene. The bare pattern graphene absorbs ~12% of the incident light (FIG. 1c) which is theoretically and experimentally enhanced to ~60% and ~45% for specific cavity lengths at λ=10 μm, respectively. A comparison between the uncoupled and the cavity-coupled systems (FIGS. 1s and 1d) shows an increase in absorption from 12% to 60%, without change in the LSP resonance frequency for all cavity modes. The FDTD simulation time was set to 5000 fs, the "auto shut-off time", which defines the convergence as $10^{-8}$ (this is very small compared to typical simulations for 3D nanostructures ($10^{-5}$)).

The monolayer graphene sheet in FDTD simulation is considered as a bulk material with thickness of 0.5 nm. This means the simulation always completely converges. Moreover, the periodic boundary condition ensures better convergence. To show the effect of "auto shut-off time" on the results, the absorption of patterned graphene for different "auto shut-off times" are overlaid in FIG. 10. For all these plots the ripples are present, which means that the ripples are not artifacts of the FDTD simulation.

The simulation for shorter time steps and the results were same. These ripples are the different modes emerging at lower wavelengths because of diffraction of surface EM waves. There is no diffraction for the incident light because the period of the pattern is less than the wavelength of the incident light. But, the wavelength of the propagating surface wave is much less than that of free space, resulting in diffractions that are seen as ripples. For graphene in an asymmetric dielectric medium, the plasmon wavenumber ($k_p$) can be calculated by means of $$\frac{\varepsilon_1}{q_{z1}} + \frac{\varepsilon_2}{q_{z2}} + 2\sigma^{intra}(\omega) = 0, \quad (1)$$

where $\varepsilon_1$ and $\varepsilon_2$ are dielectric functions of adjacent environments, $q_{z1,2} = \sqrt{\varepsilon_{1,2} - (k_p/k)^2}$ and k is the wavenumber of incident EM wave. The plasmon diffraction orders correspond to the solutions of Eq. (1), which leads to different peaks at lower wavelengths.

For analytical calculation of the optical extinction of the perforated graphene in the long wavelength limit, each element is considered as an electric dipole in the electrostatic limit with a specific polarizability $\alpha(\omega)$. The polarizability of a generalized ellipsoidal nanoparticle is $$\alpha(\omega) = \varepsilon_0 V \frac{\varepsilon - \varepsilon_m}{\varepsilon + L_e(\varepsilon - \varepsilon_m)}, \quad (2)$$

where $\varepsilon$ and $\varepsilon_m$ are the dielectric functions of the conductive element and surrounding medium, respectively. V defines the volume, and the shape factor of the ellipsoid, $L_e$, is given by:

$$L_e = \frac{abc}{2} \int_0^\infty \frac{dq}{(a^2+q)\{(q+a^2)(q+b^2)(q+c^2)\}^{\frac{1}{2}}}, \quad (3)$$

where a is the diameter of the ellipsoid along the light polarization direction, b and c are the diameters along other two dimensions. For the graphene disk array, a=b=d, where d is the disk diameter and c=t, where t is the thickness of graphene. To calculate the light absorption of perforated graphene, the light reflection/transmission of graphene disk array is used as light transmission/reflection of graphene hole array. This is an approximation to calculate the optical responsivity of perforated metal by coupled-dipole approximation (CDA) approach. Derivation of the LSP frequency is possible by calculation of the total electric potential in presence of two dimensional nanostructure elements. The total electric potential in space is due to the combination of the radiation of the graphene nanostructure and the external electric field, i.e.

$$\phi(r) = \phi^{ext}(r) - \frac{i}{\omega} \int_0^d \int_0^{2\pi} \frac{d^2 r' \nabla' \cdot \sigma(r', \omega) \nabla' \phi(r')}{|r - r'|}. \quad (4)$$

By considering homogeneous doping of graphene, it can be assumed that the conductivity does not depend on position, and outside graphene the conductivity goes to zero. It means that $\sigma(r,\omega) = F(r)\sigma(\omega)$, where F(r)=1/0 for inside/outside graphene. By defining a dimensionless variable $$\mathfrak{R} = \frac{r}{d},$$

the electric potential is given by $$\phi(r) = \phi^{ext}(r) + \mathfrak{Y} \int_0^1 \int_0^{2\pi} \frac{d^2 \mathfrak{R}' \nabla' \cdot F(\mathfrak{R}') \nabla' \phi(\mathfrak{R}')}{|\mathfrak{R} - \mathfrak{R}'|} \quad (5)$$

where $$\mathfrak{Y} = \frac{e^2 E_F}{\pi \hbar^2 \varepsilon_m d} \frac{1}{\omega(\omega + i\tau^{-1})} \quad (6)$$

Equation. (5) introduces a self-consistent potential that in absence of external potential has real eigenvalues related to the plasmonic modes. The LSP frequency is given by $$\omega_p = \frac{e}{\hbar} \sqrt{\frac{\mathfrak{X} E_F}{\pi \varepsilon_m d}} - \frac{i}{2\tau} \quad (7)$$

where $\mathfrak{X}$ is the eigenvalue of Eq. (5) and can be derived by solving this eigensystem or by using the results from the FDTD simulation. The imaginary part of $\omega_p$ is responsible for the bandwidth of the absorption peak. In addition, Eq. (7) can be applied for the graphene nanoribbon by replacing d (diameter) with w (nanoribbon width).

The lattice contribution S describes the near field and far field coupling of the electric dipoles $$S = \sum_{j \neq i} \left[ \frac{(1 - ikr_{ij})(3\cos^2 \theta_{ij} - 1)e^{ikr_{ij}}}{r_{ij}^3} + \frac{k^2 \sin^2 \theta_{ij} e^{ikr_{ij}}}{r_{ij}} \right] \quad (8)$$

where $r_{ij}$ is the distance between electric dipoles i and j, $\theta_{ij}$ is the angle between dipole j and $\vec{r}_{ij}$, and k=ω/c defines the wavenumber.

The optical reflection coefficient of the disk array can be calculated by using the polarizability and the lattice contribution $$r_{disk} = \frac{\pm i \mathfrak{C}}{\alpha^{-1} - S}, \quad (9)$$

where $$\mathfrak{C} = \frac{2\pi k}{A} \begin{cases} (\cos \vartheta)^{-1}, & s-\text{polarization} \\ \cos \vartheta, & p-\text{polarization} \end{cases} \quad (10)$$

and θ is the incident angle, which is zero in our study, A is the area of the unit cell, and positive/negative sign stands for s/p polarization. The transmission coefficient of the disk array can be obtained through $t_{disk}=1+r_{disk}$.

The absorption enhancement further depends on the electron mobility and Fermi energy of graphene, which in turn is affected by the choice of dielectric material, substrate, and gate bias. It is well known that graphene on a polymer substrate has a low carrier mobility (<1000 cm²/V·s) because of extra scattering processes. Typical scattering centers consist of charge impurities, polymers residues, and coupling centers between graphene electrons and polar or non-polar optical phonons of the polymer matrix. To study the impact of the reduced carrier mobility of patterned graphene on its absorption spectra, we performed FDTD simulations for two different carrier mobilities (μ) of 960 cm²/V·s and 250 cm²/V·s. while maintaining the same $E_F$ for the cavity-coupled system. In the FDTD simulations, the real and imaginary parts of graphene's refractive index (n,k) were calculated from the carrier mobility using the random phase approximation (RPA). In RPA, for high frequencies the complex graphene conductivity is given by $$\sigma(\omega) = \frac{e^2\omega}{i\pi\hbar^2}\left[\int_{-\infty}^{+\infty}d\varepsilon \frac{|\varepsilon|}{\omega(\omega+i\tau^{-1})}\frac{d\rho_F(\varepsilon)}{d\varepsilon} - \int_{-\infty}^{+\infty}d\varepsilon\frac{\rho_F(-\varepsilon)-\rho_F(\varepsilon)}{(\omega+i\delta)^2-4\varepsilon^2}\right] \quad (11)$$

where δ→0 is the infinitesimal parameter that is used to bypass the poles of the integral. The first and second terms correspond to the intraband electron-photon scattering processes and direct electron interband transitions, respectively. By performing the first integral, the intraband scattering is found to be similar to the Drude conductivity at low temperature $k_B T \ll E_F$ $$\sigma^{intra}(\omega) \approx i\frac{e^2 E_F}{\pi\hbar^2(\omega+i\tau^{-1})}, \quad (12)$$

where $k_B$ is the Boltzmann constant and T is the temperature. At high EM wave frequencies in the visible domain ℏω»($E_F,k_BT$) where $E_F$ is the Fermi energy with respect to the charge neutrality point (CNP) of the Dirac cone, interband transitions dominate and the light absorbance of graphene is A=πα≈2.3%, which is independent of wavelength (α≈1/137 is the fine structure constant). However, in the mid-1R frequency range and for high Fermi energy $E_F$»ℏω, graphene's optical response is dominated by intraband transitions and the conductivity (σ) follows the Drude-Lorentz model, i.e. Eq. (12), where τ is the relaxation time determined by impurity scattering ($\tau_{imp}$) and electron-phonon ($\tau_{el-ph}$) interaction time as $\tau^{-1}=\tau_{imp}^{-1}+\tau_{el-ph}^{-1}$. According to the charge conservation law, the relation of the bulk currently $J_V$ and the surface current $J_S$ for a material is given by $$\iint J_S ds = \iiint J_V dV, \quad (13)$$

which means the relation of two and three dimensional conductivity is defined by $$\sigma_{3D} = \frac{\sigma_{2D}}{t}, \quad (14)$$

where t describes the thickness of the material. The dielectric function of graphene can be obtained via its AC conductivity by means of $$\varepsilon(\omega) = \varepsilon_g + \frac{i\sigma_{3D}}{\varepsilon_0 \omega}, \quad (15)$$

where $\varepsilon_g$=2.5 is the dielectric constant of graphite. Substituting Eq. (14) into Eq. (15) gives the in-plane dielectric function of graphene, i.e.

$$\varepsilon(\omega) = \varepsilon_g + \frac{i\sigma^{intra}}{\varepsilon_0 \omega t} = \varepsilon_g - \frac{e^2 E_F}{\pi\hbar^2 \varepsilon_0 \omega(\omega+i\tau^{-1})t}, \quad (16)$$

whereas the surface-normal component is $\varepsilon_z$=2.5. The ε(ω) values calculated using Eq. (16) were used to obtain the (n,k) values for the FDTD simulations performed for different Fermi energies.

FIG. 1c shows a nominal decrease in the peak absorption from 45% to 31% as the electron mobility is decreased. For a relatively high carrier mobility (960 cm²/V·s) loss is small and therefore the bandwidth of the absorption spectrum is narrow, indicating an increased lifetime of plasmons, as observed in FIGS. 1c-1d for a cavity thickness of L=1.1 μm (this cavity thickness is chosen to show nearby high frequency weaker resonances). Higher loss in lower carrier mobility graphene gives rise to reduced plasmon lifetime and broadening of absorption spectrum, as shown in FIG. 1d. The results; from the FDTD simulations demonstrate that our device architecture can induce considerable absorption for low mobility graphene, which is a significant improvement over previously strategized devices that are functional only for high mobility graphene.

Fabrication and Experimental Results

Figure 3D:
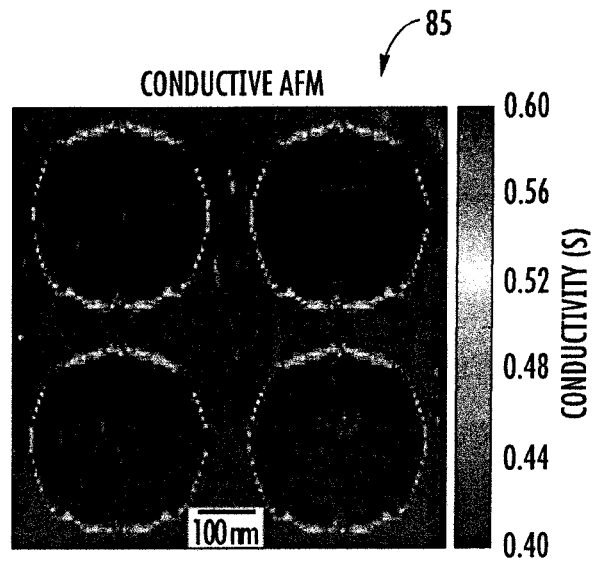
FIG. 3d is a conductive atomic-force microscopy (AFM) image of graphene nanomesh on copper foil, according to the present disclosure.

To experimentally verify the results, the cavity-coupled patterned graphene device was fabricated based on the schematic presented in FIG. 3a (see the method section for fabrication details). Large area CVD grown graphene was transferred on the substrate, and it was verified to be a monolayer by performing Raman characterization, as shown in FIG. 3b. FIGS. 3c-3d show the scanning electron microscope (SEM) image of a nanoimprinted-patterned graphene showing good uniformity in nanohole diameter across the patterned film. Furthermore, the graphene continuity and nano-pattern formation was confirmed by conductive atomic force microscopy (AFM), which shows the difference in conductivity in the holes of the patterned graphene with respect to the surrounding (FIG. 2d).

We used ion gel as the dielectric layer to electrostatically dope patterned graphene. The measured capacitance of the ion gel layer is C=2.4 pF/cm² and its absorption in mid-IR spectrum is low. The Fermi energy of graphene is given by $E_F=\hbar v_F(\pi\varphi)^{1/2}$, where $v_F\cong 10^6$ m/s is the Fermi velocity and n is the electron/hole density obtained from ρ=CΔV/, where ΔV is gate voltage relative to charge neutral point (CNP). The reported Fermi energies are calculated based on this relation. To estimate the corresponding Fermi energies experimentally, the conductivity of graphene sheet is calculated based on $\sigma(E_F)=\sigma_{min}(1+E_F^4/\Delta^4)^{1/2}$, where $\sigma_{min}$ is the minimum conductvity and Δ is the disorder strength parameter. As shown in FIGS. 11a-11b, by fitting this conductivity to the experimental data (red dotted line), $\sigma_{min}$=0.289 ms/0.371 ms and Δ=297 meV/177 meV are obtained for the diagram shown in FIGS. 11a-11b, respectively. The relation between conductivity and mobility is σ=ρeμ, where μ is the carrier mobility of graphene. Fitting this equation (green solid line) to the experimental results yields μ=250/960 cm$^2$/V·s for FIGS. 11a-11b. Positive and negative gate voltages correspond to n-doped and p-doped graphene, with a minimum conductivity occurring at the charge neutral point (CNP). According to this analysis we find that the CVD graphene sheet is p-doped during growth and transfer (~0.05 eV).

For graphene absorption measurement, we followed a well-known technique to experimentally measure the reflection spectra of thin films and 2D materials. In the experimental measurement with FTIR, we took the reflection spectrum of the structure shown in FIGS. 14-15 in supplemental material (with unpatterned graphene) as the reference such that the FTIR calibrates the spectrum as R=|r|$^2$=1 in the entire wavelength range. Following this, the reflection spectrum (R) of the structure with patterned graphene is measured with respect to the reference. Due to the presence of the back mirror, the transmission (T) is zero and hence absorption (A)=1−R−T=1−R. This directly yields the absorption measurements shown in FIGS. 5a-5b, 4a-4b which closely matches with the FDTD predicted absorption spectra.

The simulated and measured absorption of the pristine graphene, patterned graphene and cavity coupled-patterned graphene are shown in FIG. 12a and FIG. 12b, respectively. FIGS. 5a-5b shows the FDTD simulated and experimentally measured electronically tunable absorption spectra of the cavity-coupled devices for high (960 cm$^2$/V·s) (a) and low (250 cm$^2$/V·s) (b) carrier mobility graphene. The carrier mobility is influenced by the degree of oxidation and polymer residues on the graphene surface. In both cases, $E_F$ was varied between 0.7 eV to 1.0 eV. The high and low carrier mobility graphene devices exhibit a large ~2 μm and ~1 μm electrostatic tunability, respectively. The smaller peak in FIG. 5a around 7.6 μm corresponds to polymer residue, which shows the effect of impurities in graphene's optical response. An increase in the Fermi energy leads to an increase in the electron density of graphene (ρ), which strengthens the electric dipole moment generated by the LSP resonance on the nanopatterned edges and therefore enhances light absorption, as shown in FIG. 5a. As seen from FIG. 5a, there is a good agreement between Coupled Dipole Approximation (CDA) predictions, experimental measurements, and analytical graphene plasmon frequency $\omega \propto \sqrt{E_F} \propto \rho^{1/4}$. According to the experimental absorption spectra, the plasmon lifetimes ($\tau_{PL}=\hbar\Gamma^{-1}$) for high (960 cm$^2$/V·s) and low (250 cm$^2$/V·s) carrier mobility graphene are determined to be $\tau_{PL(high)} \approx 38$ fs and $\tau_{PL(low)} \approx 16$ fs, respectively, which is compatible with the momentum relaxation time (τ).

Plasmon-Phonon Coupling

While the theoretical prediction using the FDTD method is in excellent agreement with the LSP peak locations ($\omega_0$) in the experimental curves (FIG. 4b), it fails to explain the asymmetric line-shape of the resonance. Hence, we can infer that in our device the effective combination of SU-8 polymer and the ion-gel matrix behaves as a polar substrate. Polar materials have ions of different valence, whose oscillating dipole moment gives rise to the interaction between electrons and optical phonons-called the Fröhlich interaction. The surface optical phonons in polar substrates are Fuchs-Kliewer like. By placing graphene on a polar substrate the long range Fröhlich interaction mediates the interaction between optical phonons and surface plasmons in graphene. The interaction between polar substrate/graphene phonons and electrons in graphene modifies substantially the graphene plasmon dispersion relation. The white dotted line in FIG. 4a represents the plasma frequency of graphene.

The Dynamic Polarizability $$\chi(q, i\omega_n) = -\frac{1}{A}\int_0^\beta d\tau\, e^{i\omega_n\tau}\langle T\rho_q(\tau)\rho_{-q}(0)\rangle, \quad (17)$$

determines several important quantities, such as effective electron-electron interaction, plasmon and phonon spectra, and Friedel oscillations.

$$\omega_n = \frac{2\pi n}{\beta}$$

are Matsubara frequencies, T is time ordering operator, $\beta=1/k_BT$, where $k_B$ is the Boltzmann constant, and n is an integer number. $\rho_q$ is the density operator in q-space and A denotes the area of the sample. This quantity is calculated in the canonical ensemble for both of the sub-lattice density operators ($\rho=\rho_a+\rho_b$). The dynamic polarizability in the RPA regime is given by $$\chi^{RPA}(q, \omega) = \frac{\chi^0(q, \omega)}{\varepsilon^{RPA}(q, \omega)}, \quad (18)$$

where $\chi^0(q,\omega)$ is the non-interacting (zeroth order) polarizability (single pair bubble) and $\varepsilon^{RPA}(q,\omega)=\varepsilon_m-v_c(q)\chi^0(q,\omega)$, with $\varepsilon_m$ being the permittivity of the environment and $v_c(q)=e^2/2\varepsilon_0 q$ the Coulomb interaction between the carriers. The RPA method corresponds to the expansion of $1/\varepsilon^{RPA}(q,\omega)$, leading to an infinite power series over the bubble diagrams. If optical phonons are also considered, the effective dielectric function in the RPA expansion takes the form $$\varepsilon^{RPA}(q, \omega) = \varepsilon_m - v_c(q)\chi^0(q, w) - \quad (19)$$
$$\varepsilon_m \sum_l v_{sph,l}(q, \omega)\chi^0(q, \omega) - \varepsilon_m v_{oph}(q, \omega)\chi^0_{j,j}(q, \omega).$$

The third term is the effective dielectric function for different phonon modes (l) coming from the electron-electron interaction mediated by substrate optical phonons, which couple to the electrons by means of the Fröhlich interaction, $V_{sph,l}(q,\omega)=|M_{sph}|^2 G_1^0(\omega)$, where $|M_{sph}|^2$ is the scattering and $G_1^0$ is the free phonon Green's function. The last term of Eq. (19) corresponds to graphene's optical phonon mediated electron-electron interaction, $v_{oph}(q,\omega)=|M_{oph}|^2 G^0(\omega)$. Here $|M_{oph}|^2$ defines the scattering matrix element and $G^0(\omega)$ is the free phonon Green's function. In Eq. (19), $\chi_{i,j}^0(q,\omega)$ is the current-current correlation function. By taking the decay rate $\omega \rightarrow \omega+i\tau^{-1}$ into account, the dynamic polarizability reduces to $\chi^0(q,\omega) \approx E_F q^2/\pi\hbar^2(\omega+i\tau^{-1})^2$. The momentum relaxation time (τ) can be derived by considering the impurity, electron-phonon interaction and the scattering related to nanostructure edges $\tau=\tau_{DC}^{-1}\tau_{edge}^{-1}\tau_{e-ph}^{-1}$, which determines the plasmon lifetime and the absorption spectrum bandwidth. It can be evaluated via the measured DC mobility p of the graphene sample using $\tau_{DC}=\mu\hbar\sqrt{\pi\rho}/ev_F$, where $v_F\sim10^6$ m/s is the Fermi velocity and $\rho=(E_F/\hbar v_F)^2/\pi$ is the charge carrier density. $\tau_{edge}\approx(1\times10^6/w-w_0)^{-1}$ is due to the scattering from the nanostructure edges, where W is the edge-to-edge distance of the holes, $w_0\approx7$ nm is the parameter that includes edge effects, and $\tau_{e-ph}=\hbar/2$ Im($\Sigma_{e-ph}$) is related to the scattering because of electron-phonon coupling. Im($\Sigma_{e-ph}$)=$\gamma|\hbar\omega-\text{sgn}(\hbar\omega-E_F)\hbar\omega_{oph}|$, where $E_{e-ph}$ is the electron self-energy, $\gamma=18.3\times10^{-3}$ is a dimensionless constant describing the electron-phonon coupling coefficient, and $\hbar\omega_{oph}\approx0.2$ eV is the graphene optical phonon energy. From this it is evident that the plasmon lifetime is reduced due to the electron-phonon interaction and edge scattering, but the DC conductivity which is used to calculate the dielectric function of graphene is invariant if the edge-to-edge distance of the pattern is more than the carrier mean free path ($L_{MFP}=v_F\tau_{DC}$). The modified Drude model is not valid for a patterned graphene sheet only if the edge-to-edge distance is much smaller than the carrier mean free path of electrons and holes. For the chosen pattern and carrier mobility (p=960 cm$^2$/V·s), the carrier mean free path ($L_{MFP}=v_F\tau_{DC}$<42 nm) is smaller than the edge-to-edge distance (=70 nm), which means that the modified Drude model is a good approximation for the dielectric function of this patterned graphene sheet. In presence of hard boundaries, atomic displacement vanishes at the boundaries, thereby modifying the acoustic and optical phonon dispersion. This means we need to consider a graphene nanoribbon (GNR) with zigzag-edge or armchair-edge and N periods (N is the number atoms between two edges) with several quantized vibration modes. This model is applied in the long wavelength limit; therefore only the lowest vibration modes up to N/2 appear. By applying the boundary conditions to the displacement equation, the longitudinal (LO) and transverse (TO) optical phonon branches are changed, i.e. $\omega_n^2=\omega_{LO}^2-\lambda^2(q_n^2+q^2)^2+\beta_L^2(q_n^2+q^2)$ and $\omega_n^2=\omega_{TO}^2-\beta_T^2(q_n^2+q^2)$. This n TO means the optical phonon frequency, which is almost the same for both branches (LO and TO), shifts from $\omega_{op}\sim1581$ cm$^{-1}$ to $\omega_{op}\sim1591$ cm$^{-1}$ for both zigzag-edge and armchair-edge GNR. We used this modified optical phonon frequency in FIGS. 4a-4b. The effect of this change is very small.

The coupling of plasmon and substrate/graphene phonon can be characterized through the loss function (Z), which is the imaginary part of inverse effective dielectric function calculated via the generalized RPA theory $$Z \propto -\text{Im}\left(\frac{1}{\varepsilon^{RPA}}\right). \quad (20)$$

The loss function represents the amount of energy dissipated by exciting the plasmon coupled to the substrate and optical phonons in graphene. The surface plasmons in graphene are damped through radiative and nonradiative processes. Nonradiative damping transfers the plasmon energy to hot electron-hole excitation by means of intraband transition. FIG. 4a shows the loss function for graphene with carrier mobility $\mu$=960 cm2/V·s and $E_F$=1.0 eV. The thickness of the optical cavity is chosen to be 1.1 μm such that the first ($\omega_0$) and second ($\omega_2$) modes lead to 44% and 33% light absorption, respectively. The plasmon assisted electron-hole pair generation in this structure lies outside the Landau intraband damping region, indicated by the shaded area in FIG. 4a. A band gap in the plasmon-phonon dispersion relation is formed via Fröhlich interaction between graphene plasmons and optical phonons. This coupling leads to the splitting of the energy into two distinct branches: surface plasmon phonon polaritons (SPPPs) and graphene plasmons (GPs). The horizontal branch line marked as $\omega_0$ is the LSP mode in FIGS. 1a and 1s independent of the plasmon wavevector due to the localization of the LSP. The asymmetric line shape of the first band ($\omega_0$) in FIG. 1c, which is observed in experiments, is due to the merging of these two bands (LSP and SPPP). FIG. 4a shows a clear blue shift in the GP band at a wavevector ($k_{sp}\approx5.5\times10^5$ cm$^{-1}$), corresponding to the edge-to-edge distance between the holes in presence of edge effect. Interestingly, there exists a discrepancy in the location of the second mode peak of the FDTD curve simulated without accounting for optical phonons ($\omega_1$) from that of the experimental spectrum ($\omega_2$). This is attributed to the plasmon-phonon coupling, and we show that by inserting the plasmon-phonon interaction as a perturbation and using $\varepsilon^{PA}(q,\omega)$ in Eq. (19) as effective graphene dielectric function in the FDTD simulations, one can recover the experimentally observed blue shift, as illustrated in FIG. 4b by the green dotted line. The simple Drude model cannot capture the plasmon-phonon interactions which leads to discrepancies between FDTD predictions and experimental measurements as can be observed in FIG. 4b. In the long wavelength regime, by substituting $\chi^0(q,\omega)\approx E_F q^2/\pi\hbar^2(\omega+i\tau^{-1})^2$ and $v_c$ into Eq. (19), the second term on the right-hand side is reduced to the Drude model dielectric function $$\varepsilon_{Drude} = -v_c(q)\chi^0(q,\omega) = -\frac{e^2 E_f q}{2\varepsilon_0\pi\hbar^2(\omega+i\tau^{-1})^2}.$$

(21)

According to Eq. (21), the in-plane momentum of the pristine graphene should be equal to $$q = \frac{2}{l}.$$

In Eq. (19), the phonon terms, which are small relative to $\varepsilon^{Drude}$, perturb the original system. In order to include the electron-phonon coupling in the simulation and to predict the experimental results with higher accuracy, Eq. (19) has been used as the input data in the FDTD simulations to generate the plasmon-phonon dispersion diagram of FIG. 4b with much improved correspondence between prediction and experimental observation. This analysis explains different processes involved in the experimental results and the physical optoelectronic phenomena and highlights the plasmon-phonon interaction leads to the hybridization of the plasmon dispersion relation, which gives rise to a blue shift in the propagating surface plasmon spectrum. However, the main absorption peak ($w_0$), which originates from LSP, remains unperturbed due to frequency domain separation between the phonon and LSP resonances.

Conclusion

In conclusion, we have presented a scheme to increase the light-graphene interaction by the direct excitation of plasmons on patterned monolayer graphene coupled to an optical cavity. Our design of a square lattice of holes on graphene, which is experimentally realized following a simple nanoimprinting technique, not only preserves material continuity for electronic conductivity, which is essential for optoelectronic devices, but also leads to direct plasmon excitation that is independent of the incident light polarization. Therefore, our design outperforms other nanoribbon based devices whose absorption is polarization-dependent, thereby reducing their performance for unpolarized light. This approach triggers the direct excitation of cavity-coupled plasmon in CVD grown monolayer graphene with a cavity thickness of L=1.1 µm and yields an experimentally observed absorption of ~45%, which is the highest value reported so far in the 8-12 µm band. We show that a reduction in carrier mobility of graphene decreases the absorption to ~30%, which is nonetheless higher than previous studies. Furthermore, electronically controlled dynamic tunability (~2 µm) is successfully demonstrated. We have shown experimentally and theoretically that the carrier mobility of graphene, which is influenced by the defect density, determines the enhanced absorption bandwidth and line-shape. Further, CVD grown graphene quality, pattern, gating optimizations, and alternative low-absorbance dielectrics as gating materials are needed in order to reach the theoretical maximum absorption of ~60% for a cavity thickness of L=1.6 µm. Such voltage tunable high absorption in monolayer graphene will enable the development of various practical graphene based optoelectronic devices like photodetectors, sensors, modulators, etc.

Method Section: Device Fabrication Process

The graphene sheet is grown on a 25 µm thick copper foil in an oven composed of a molten silica tube heated in a split tube furnace. The molten silica tube and copper foil are loaded inside the furnace, evacuated, back filled with hydrogen, and heated up to 1000° C. while keeping a 50 sccm $H_2$ stream. The subsequent steps include reinstating the copper foil at 1000° C. for 30 minutes, inserting 80 sccm of $CH_4$ for 30 minutes. Then the furnace is cooled down to room temperature without gas feeding. An optically thick layer of Cr/Au (4 nm/200 nm) is deposited on a glass substrate as a back reflector using e-beam deposition. A photoresist (SU-8) layer is spin-coated on the gold back reflector to form an optical cavity, that is cured under UV lamp for 2 hours and baked on a hot plate for 1 hour at 95° C. in order to complete the cross-linking process. A thin layer (~20 nm) of Gold-Palladium (Au—Pd) is sputtered on the dielectric spacer which function as a gate electrode. A CVD-grown graphene sheet is transferred onto the Au—Pd layer using a PMMA transfer layer which is subsequently dissolved in Acetone. The square lattice hole pattern is fabricated following a simple large area nanoimprinting technique.

A poly dimethylsiloxane (PDMS) stamp is embossed against a thin photoresist (SU-8) layer that is spun coated on the graphene layer, followed by reactive ion etcher (RIE) in order to perforate the graphene layer. Low carrier mobility nanomesh graphene is prepared by rinsing the residual polymers (PMMA and SU-8) in acetone one time for a few seconds. In contrast, the high carrier mobility sample is prepared by repeating this process for more than ten times in order to reduce plolymer residues from the perforated graphene. A high capacitance ion gel film with refractive index of 1.3 is drop-casted on graphene in order to tune its Fermi energy to high values (~1 eV). Ion gel is a printable gate dielectric polymer made by mixing ionic liquid ([EMIM] [TFSI]) (Sigma-Aldrich, Inc.) with dry PS-PEO-PS (10-44-10 kg/mol) triblock copolymer (Polymer Source, Inc.) with ratio 1:0.04 in a dry solvent (dichloromethane) (Sigma-Aldrich, Inc.) and by stirring the mixture overnight. Then it is left for 48 hours inside high vacuum chamber (pressure<$10^{-6}$ torr) in order to evaporate the remaining solvent. The materials are dried in high vacuum for 24 hours then transferred to the glovebox for 4 days. The gate is fabricated by depositing Cr/Au (3 nm/40 nm) on Si substrate. A copper wire is connected to the gate by applying silver paste on the side and back. The resulting substrate is flipped upside down and put on top of the ion gel.

Materials Characterization and Measurement

After RIE and the polymer removal, conductive AFM was used to confirm the presence of a patterned graphene layer on the substrate. After patterning the graphene on copper foil following the same procedure and parameters used to pattern the graphene sheet on the SU-8 layer, conductive AFM (MultiMode, Atomic Force Microscope, Nanoscope III, Digital Instruments, Santa Barbara, Calif.) is employed to map of conductivity of the patterned graphene with nanoscale spatial resolution. Conductive (Au coated) cantilevers with spring constant k=0.06 N/m was used. Measurements are performed in contact mode and a full IV curve was collected at each pixel of the image. The theoretical simulations are done by finite-difference time-domain (FDTD) method using Lumerical FDTD (Lumerical Inc.) software. The Raman spectrum of the grown graphene sheet is measured by WITec Renishaw RM 1000B Micro-Raman Spectrometer with an excitation laser wavelength of 514 nm and a 50× objective lens. The real and imaginary parts of the gold dielectric function used in simulations are taken from Palik. The corresponding optical absorption measurements are performed with a microscope-coupled FTIR (Bruker Inc., Hyperion 1000-Vertex 80). The mobility is measured by using the model 2450 SourceMeter® SMU instrument and a four-point probe. We applied the gate voltage between bottom and top gate with ion gel as dielectric in presence of "patterned graphene" with two probes and measured the electrical conductivity through source-drain using other probes.

References (all References are hereby incorporated by reference in their entirety)

1 Bonaccorso, F., Sun, Z., Hasan, T. & Ferrari, A. C. Graphene photonics and optoelectronics. *Nature Photonics* 4, 611-622, doi:Doi 10.1038/Nphoton.2010.186 (2010).

2 Falkovsky, L. A. Optical properties of doped graphene layers. *Journal of Experimental and Theoretical Physics* 106, 575-580, doi:Doi 10.1134/S1063776108030175 (2008).

3 Falkovsky, L. A. & Pershoguba, S. S. Optical far-infrared properties of a graphene monolayer and multilayer. *Physical Review B* 76, doi:Artn 153410 Doi 10.1103/Physrevb.76.153410 (2007).

4 Falkovsky, L. A. & Varlamov, A. A. Space-time dispersion of graphene conductivity. *Eur Phys J B* 56, 281-284, doi:DOI 10.1140/epjb/e2007-00142-3 (2007).

5 Singh, V., Joung, D., Zhai, L., Das, S., Khondaker, S. I. & Seal, S. Graphene based materials: Past, present and future. *Progress in Materials Science* 56, 1178-1271, doi:DOI 10.1016/j.pmatsci.2011.03.003 (2011).

6 Schwierz, F. Graphene transistors. *Nature nanotechnology* 5, 487-496, doi:10.1038/nnano.2010.89 (2010).

7 Gan, X., Shiue, R. J., Gao, Y., Mak, K. F., Yao, X., Li, L., Szep, A., Walker, D., Jr., Hone, J., Heinz, T. F. & Englund, D. High-contrast electrooptic modulation of a photonic crystal nanocavity by electrical gating of graphene. *Nano Lett* 13, 691-696, doi:10.1021/n1304357u (2013).

8 Yao, Y., Shankar, R., Kats, M. A., Song, Y., Kong, J., Loncar, M. & Capasso, F. Electrically tunable metasurface perfect absorbers for ultrathin mid-infrared optical modulators. *Nano Lett* 14, 6526-6532, doi:10.1021/n1503104n (2014).

9 Liu, M., Yin, X., Ulin-Avila, E., Geng, B., Zentgraf, T., Ju, L., Wang, F. & Zhang, X. A graphene-based broadband optical modulator. *Nature* 474, 64-67, doi:10.1038/nature10067 (2011).

10 Sun, Z. & Chang, H. Graphene and graphene-like two-dimensional materials in photodetection: mechanisms and methodology. *ACS nano* 8, 4133-4156, doi:10.1021/nn500508c (2014).

11 Liu, Z., Lau, S. P. & Yan, F. Functionalized graphene and other two-dimensional materials for photovoltaic devices: device design and processing. *Chemical Society reviews*, doi:10.1039/c4cs00455h (2015).

12 Sun, Z., Hasan, T., Torrisi, F., Popa, D., Privitera, G., Wang, F., Bonaccorso, F., Basko, D. M. & Ferrari, A. C. Graphene mode-locked ultrafast laser. *ACS nano* 4, 803-810, doi:10.1021/nn901703e (2010).

13 Ju, L., Geng, B., Horng, J., Girit, C., Martin, M., Hao, Z., Bechtel, H. A., Liang, X., Zettl, A., Shen, Y. R. & Wang, F. Graphene plasmonics for tunable terahertz metamaterials. *Nature nanotechnology* 6, 630-634, doi:10.1038/nnano.2011.146 (2011).

14 Yan, H. G., Low, T., Zhu, W. J., Wu, Y. Q., Freitag, M., Li, X. S., Guinea, F., Avouris, P. & Xia, F. N. Damping pathways of mid-infrared plasmons in graphene nanostructures. *Nature Photonics* 7, 394-399, doi:Doi 10.1038/Nphoton.2013.57 (2013).

15 Brar, V. W., Jang, M. S., Sherrott, M., Lopez, J. J. & Atwater, H. A. Highly confined tunable mid-infrared plasmonics in graphene nanoresonators. *Nano Lett* 13, 2541-2547, doi:10.1021/nl400601c (2013).

16 Fang, Z., Wang, Y., Schlather, A. E., Liu, Z., Ajayan, P. M., de Abajo, F. J., Nordlander, P., Zhu, X. & Halas, N. J. Active tunable absorption enhancement with graphene nanodisk arrays. *Nano Lett* 14, 299-304, doi:10.1021/nl404042h (2014).

17 Fang, Z., Thongrattanasiri, S., Schlather, A., Liu, Z., Ma, L., Wang, Y., Ajayan, P. M., Nordlander, P., Halas, N. J. & Garcia de Abajo, F. J. Gated tunability and hybridization of localized plasmons in nanostructured graphene. *ACS nano* 7, 2388-2395, doi:10.1021/nn3055835 (2013).

18 Furchi, M., Urich, A., Pospischil, A., Lilley, G., Unterrainer, K., Detz, H., Kiang, P., Andrews, A. M., Schrenk, W., Strasser, G. & Mueller, T. Microcavity-integrated graphene photodetector. *Nano Lett* 12, 2773-2777, doi: 10.1021/nl204512x (2012).

19 Otsuji, T., Popov, V. & Ryzhii, V. Active graphene plasmonics for terahertz device applications. *J Phys D Appl Phys* 47, 094006 (2014).

20 Zhang, Y., Feng, Y., Zhu, B., Zhao, J. & Jiang, T. Graphene based tunable metamaterial absorber and polarization modulation in terahertz frequency. *Optics express* 22, 22743-22752, doi:10.1364/OE.22.022743 (2014).

21 Majumdar, A., Kim, J., Vuckovic, J. & Wang, F. Graphene for Tunable Nanophotonic Resonators. *Ieee J Sel Top Quant* 20, doi:Artn 4600204 Doi 10.1109/Jstqe.2013.2273413 (2014).

22 Jablan, M., Buljan, H. & Soljacic, M. Plasmonics in graphene at infrared frequencies. *Physical Review B* 80, doi:Artn 245435 Doi 10.1103/Physrevb.80.245435 (2009).

23 Weiglhofer, W. S., Lakhtakia, A. & Michel, B. Maxwell Garnett and Bruggeman formalisms for a particulate composite with bianisotropic host medium (vol 15, pg 263, 1997). *Microwave and Optical Technology Letters* 22, 221-221, doi:Doi 10.1002/(Sici)1098-2760(19990805)22:3<221::Aid-Mop21>3.0.Co;2-R (1999).

24 Granqvist, C. G. & Hunderi, O. Conductivity of Inhomogeneous Materials—Effective-Medium Theory with Dipole-Dipole Interaction. *Physical Review B* 18, 1554-1561, doi:DOI 10.1103/PhysRevB.18.1554 (1978).

25 Thongrattanasiri, S., Koppens, F. H. & Garcia de Abajo, F. J. Complete optical absorption in periodically patterned graphene. *Phys Rev Lett* 108, 047401, doi:10.1103/PhysRevLett.108.047401 (2012).

26 Chen, J. H., Cullen, W. G., Jang, C., Fuhrer, M. S. & Williams, E. D. Defect scattering in graphene. *Phys Rev Lett* 102, 236805, doi:10.1103/PhysRevLett.102.236805 (2009).

27 Dean, C. R., Young, A. F., Meric, I., Lee, C., Wang, L., Sorgenfrei, S., Watanabe, K., Taniguchi, T., Kim, P., Shepard, K. L. & Hone, J. Boron nitride substrates for high-quality graphene electronics. *Nature nanotechnology* 5, 722-726, doi:10.1038/nnano.2010.172 (2010).

28 Hirai, H., Tsuchiya, H., Kamakura, Y., Mori, N. & Ogawa, M. Electron mobility calculation for graphene on substrates. *Journal of Applied Physics* 116, 083703, doi: Artn 083703 Doi 10.1063/1.4893650 (2014).

29 Song, H. S., Li, S. L., Miyazaki, H., Sato, S., Hayashi, K., Yamada, A., Yokoyama, N. & Tsukagoshi, K. Origin of the relatively low transport mobility of graphene grown through chemical vapor deposition. *Scientific reports* 2, 337, doi:10.1038/srep00337 (2012).

30 Hwang, J. Y., Kuo, C. C., Chen, L. C. & Chen, K. H. Correlating defect density with carrier mobility in large-scaled graphene films: Raman spectral signatures for the estimation of defect density. *Nanotechnology* 21, 465705, doi:10.1088/0957-4484/21/46/465705 (2010).

31 Ferrari, A. C., Meyer, J. C., Scardaci, V., Casiraghi, C., Lazzeri, M., Mauri, F., Piscanec, S., Jiang, D., Novoselov, K. S., Roth, S. & Geim, A. K. Raman spectrum of graphene and graphene layers. *Phys Rev Lett* 97, 187401, doi:10.1103/PhysRevLett.97.187401 (2006).

32 Gupta, A., Chen, G., Joshi, P., Tadigadapa, S. & Eklund, P. C. Raman scattering from high-frequency phonons in supported n-graphene layer films. *Nano Lett* 6, 2667-2673, doi:10.1021/nl061420a (2006).

33 Hwang, E. H., Sensarma, R. & Das Sarma, S. Plasmon-phonon coupling in graphene. *Physical Review B* 82, doi:Artn 195406 Doi 10.1103/Physrevb.82.195406 (2010).

34 Jalabert, R. & Das Sarma, S. Quasiparticle properties of a coupled two-dimensional electron-phonon system. *Physical review. B, Condensed matter* 40, 9723-9737, doi:10.1103/PhysRevB.40.9723 (1989).

35 Wunsch, B., Stauber, T., Sols, F. & Guinea, F. Dynamical polarization of graphene at finite doping. *New Journal of Physics* 8, 318-318, doi:Artn 318 Pii 51367-2630(06)35560-7 Doi 10.1088/1367-2630/8/12/318 (2006).

36 Mikhailov, S. A. & Savostianova, N. A. Microwave response of a two-dimensional electron stripe. *Physical Review B* 71, doi:Artn 035320 Doi 10.1103/Physrevb.71.035320 (2005).

37 Stern, F. Polarizability of a Two-Dimensional Electron Gas. *Physical Review Letters* 18, 546-548, doi:10.1103/PhysRevLett.18.546 (1967).

38 Gerald, M. D. *Many-Particle Physics*. Third Edition edn, (Kluwer Academic/Plenum publisher, 2000).

39 Hwang, E. H. & Das Sarma, S. Dielectric function, screening, and plasmons in two-dimensional graphene. *Physical Review B* 75, doi:Artn 205418 Doi 10.1103/Physrevb.75.205418 (2007).

40 Chanda, D., Shigeta, K., Gupta, S., Cain, T., Carlson, A., Mihi, A., Baca, A. J., Bogart, G. R., Braun, P. & Rogers, J. A. Large-area flexible 3D optical negative index metamaterial formed by nanotransfer printing. *Nature nanotechnology* 6, 402-407, doi:10.1038/nnano.2011.82 (2011).

41 Chanda, D., Shigeta, K., Truong, T., Lui, E., Mihi, A., Schulmerich, M., Braun, P. V., Bhargava, R. & Rogers, J. A. Coupling of plasmonic and optical cavity modes in quasi-three-dimensional plasmonic crystals. *Nature communications* 2, 479, doi:10.1038/ncomms1487 (2011).

42 Weingartner, H., Sasisanker, P., Daguenet, C., Dyson, P. J., Krossing, I., Slattery, J. M. & Schubert, T. The dielectric response of room-temperature ionic liquids: effect of cation variation. *J Phys Chem B* 111, 4775-4780, doi: 10.1021/jp0671188 (2007).

43 Cho, J. H., Lee, J., Xia, Y., Kim, B., He, Y., Renn, M. J., Lodge, T. P. & Frisbie, C. D. Printable ion-gel gate dielectrics for low-voltage polymer thin-film transistors on plastic. *Nature materials* 7, 900-906, doi:10.1038/nmat2291 (2008).

44 Palik, E. D. Handbook of Optical-Constants. *J Opt Soc Am A* 1, 1297-1297 (1984).

45 Song, J. C.; Rudner, M. S.; Marcus, C. M.; Levitov, L. S. Nano Lett, 11, (11), 4688-92 (2011).

Many modifications and other embodiments of the present disclosure will come to the mind of one skilled in the art having the benefit of the teachings presented in the foregoing descriptions and the associated drawings. Therefore, it is understood that the present disclosure is not to be limited to the specific embodiments disclosed, and that modifications and embodiments are intended to be included within the scope of the appended claims.

That which is claimed is:

1. An optical detector device comprising:
a substrate;
a reflector layer carried by said substrate;
a first dielectric layer over said reflector layer;
a graphene layer over said first dielectric layer and having a perforated pattern therein;
the perforated pattern comprising an array of openings, the array of openings comprising a plurality of rows and a plurality of columns; and
a second dielectric layer over said graphene layer and covering said array of openings.

2. The optical detector device of claim 1 wherein the array of openings comprises a square array of openings.

3. The optical detector device of claim 2 wherein each of the openings is circle-shaped.

4. The optical detector device of claim 1 wherein the perforated pattern is symmetrical.

5. The optical detector device of claim 1 wherein said first dielectric layer comprises a polymer material.

6. The optical detector device of claim 1 wherein said graphene layer comprises a monolayer of graphene.

7. The optical detector device of claim 1 further comprising:
a first electrically conductive contact coupled to said second dielectric layer; and
a second electrically conductive contact coupled to said graphene layer.

8. The optical detector device of claim 1 wherein said reflector layer comprises gold material.

9. The optical detector device of claim 1 wherein said reflector layer has a thickness greater than a threshold thickness for optical opacity.

10. An optical detector device comprising:
a substrate;
a gold reflector layer carried by said substrate;
a first dielectric layer over said gold reflector layer;
a graphene layer over said first dielectric layer and having a perforated pattern defining a square array of openings;
the perforated pattern comprising an array of openings, the array of openings comprising a plurality of rows and a plurality of columns;
a second dielectric layer over said graphene layer and covering said array of openings;
a first electrically conductive contact coupled to said second dielectric layer; and
a second electrically conductive contact coupled to said graphene layer.

11. The optical detector device of claim 10 wherein each of the openings is circle-shaped.

12. The optical detector device of claim 10 wherein the perforated pattern is symmetrical.

13. The optical detector device of claim 10 wherein said first dielectric layer comprises a polymer material.

14. The optical detector device of claim 10 wherein said graphene layer comprises a monolayer of graphene.

15. The optical detector device of claim 10 wherein said gold reflector layer has a thickness greater than a threshold thickness for optical opacity.

16. An optical detector device comprising:
a substrate;
a reflector layer carried by said substrate;
a first dielectric layer over said reflector layer;
a graphene layer over said first dielectric layer and having a perforated pattern therein;
the perforated pattern comprising an array of openings; and
a second dielectric layer over said graphene layer and covering said array of openings.

17. The optical detector device of claim 16 wherein the array of openings comprises a square array of openings.

18. The optical detector device of claim 17 wherein each of the openings is circle-shaped.

19. The optical detector device of claim 16 wherein the perforated pattern is symmetrical.

20. The optical detector device of claim 1 wherein said second dielectric layer comprises an ion-gel dielectric layer.

* * * * *